United States Patent
Vajdic et al.

(10) Patent No.: US 8,311,618 B2
(45) Date of Patent: Nov. 13, 2012

(54) METHOD AND APPARATUS FOR QUANTITATIVE ASSESSMENT OF CARDIAC ELECTRICAL EVENTS

(75) Inventors: Branislav Vajdic, Monte Sereno, CA (US); Alexander D. Lunginovic, Saratoga, CA (US); Ljupco Hadzievski, Belgrade (RS); Bosko Bojovic, Belgrade (RS)

(73) Assignee: New Cardio, Inc., Santa Clara, CA (US)

( * ) Notice: Subject to any disclaimer, the term of this patent is extended or adjusted under 35 U.S.C. 154(b) by 0 days.

(21) Appl. No.: 12/983,451

(22) Filed: Jan. 3, 2011

(65) Prior Publication Data

US 2011/0118616 A1    May 19, 2011

Related U.S. Application Data

(62) Division of application No. 12/184,068, filed on Jul. 31, 2008, now Pat. No. 8,209,002.

(60) Provisional application No. 60/963,065, filed on Aug. 1, 2007.

(51) Int. Cl.
*A61N 5/02* (2006.01)
*A61N 5/04* (2006.01)

(52) U.S. Cl. ........ 600/512; 600/508; 600/509; 600/513; 600/516

(58) Field of Classification Search .......... 600/508–509, 600/512–516
See application file for complete search history.

(56) References Cited

U.S. PATENT DOCUMENTS

| | | | |
|---|---|---|---|
| 4,850,370 A | 7/1989 | Dower | |
| 5,458,116 A | 10/1995 | Egler | |
| 5,711,304 A | 1/1998 | Dower | |
| 6,128,526 A | 10/2000 | Stadler et al. | |
| 7,266,408 B2 | 9/2007 | Bojovic et al. | |
| 7,751,875 B2 | 7/2010 | Bojovic et al. | |
| 2004/0176696 A1* | 9/2004 | Mortara | 600/515 |

FOREIGN PATENT DOCUMENTS

| | | |
|---|---|---|
| WO | WO 96/24905 | 8/1996 |
| WO | WO 00/14687 | 3/2000 |
| WO | WO 03/057031 | 7/2003 |
| WO | WO 2005/072607 | 8/2005 |

OTHER PUBLICATIONS

Abramowitcz, M. et al., eds. (1972). *Handbook of Mathematical Functions with Formulas, Graphs, and Mathematical Tables*, Dover Publications: New York, NY, pp. VII-VIII. (Table of Contents Only, downloaded from National Bureau of Standards, US Government Printing Office, Washington, DC, 20402).

(Continued)

*Primary Examiner* — Nicole F Lavert

(57) ABSTRACT

Method and apparatus for computer enabled analysis of ECG (electro cardiographic) data by exploiting computerized three-dimensional spatial presentation of the measured data using vectors. A three-dimensional presentation of the human heart may be correlated with waveforms specific for standard ECG or derived ECG signals based on the dipole approximation of the heart electrical activity. Additional tools for analyzing ECG data are also provided which may be used to determine the time of cardiac electrical events, to select specific beats for automated cardiac interval determination, and to flag ECGs that have been evaluated by automated means but may benefit by human reading.

11 Claims, 12 Drawing Sheets

OTHER PUBLICATIONS

Anderson, M.E. et al. (Nov. 2002). "Cardiac Repolarization: Current Knowledge, Critical Gaps, and New Approaches to Drug Development and patent Management," presented at *Duke Clinical Research Institute/American Heart Journal Expert Meeting on Repolarization Changes*, Rockville, MD, Aug. 9-11, 2000, *Am. Heart J.* 144(5):769-781.

Anonymous. (Oct. 2005). "Guidance for Industry: E14 Clinical Evaluation of QT/QTc Interval Prolongation and Proarrhythmic Potential for Non-Antiarrhythmic Drugs," located at http://www.fda.gov/cder/guidance/6922fnl.pdf, 20 pages.

Antman, E.M. et al. (2004). "ACC/AHA Guidelines for the Management of Patients with ST-Elevation Myocardial Infarction," located at www.acc.org/guidelines/stemi/index.pdf, last accessed on Aug. 10, 2005, pp. e1-e212.

Antzelevitch, C. (Nov. 2003). "Molecular Genetics of Arrhythmias and Cardiovascular Conditions Associated with Arrhythmias," *J. Cardiovasc. Electrophysiol.* 14(11):1259-1272.

Braunwald, E. et al. (Oct. 2, 2002). "ACC/AHA 2002 Guideline Update for the Management of Patients with Unstable Angina and Non-ST-Segment Elevation Myocardial Infarction—Summary Article," *J. Am. Coll. Cardiol.* 40(7):1366-1374.

Burger, H.C. et al. (1948). "Heart-Vector and Leads. Part III. Geometrical Representation," *Br. Heart J.* 10:229-233.

Cain, M.E. et al. (Jan. 1996). "ACC Expert Consensus Document: Signal Averaged Electrocardiography," *J. Am. Coll. Cardiol.* 27(1):238-249.

Cohen, I. et al. (Aug. 19, 1976). "Cellular Basis for the T Wave of the Electrocardiogram," *Nature* 262(5570):657-661.

Edenbrandt, L. et al. (1988). "Vectorcardiogram Synthesized From a 12-Lead ECG: Superiority of the Inverse Dower Matrix," *J. Electrocardiol.* 21(4):361-367.

Examination Report mailed Aug. 4, 2008, for EP Patent Application No. 05705714.3 filed Jan. 14, 2005, six pages.

Fisch, C. (Nov. 15, 2000). "Centennial of the String Galavanometer and the Electrocardiogram," *J. Am. Coll. Cardiol.* 36(6):1737-1745.

Frank, E. (May 1956). "An Accurate, Clinically Practical System for Spatial Vectorcardiography," *Circulation* 13:737-749.

Hnatkova, K. et al. (1994). "Adjustments of QT Dispersion Assessed from 12 Lead Electrocardiograms for Different Numbers of Analysed Electrocardiographic Leads: Comparison of Stability of Different Methods," *Br. Heart J.* 72:390-396.

Hurst, J.W. (Jun. 1997). "Abnormalities of the S-T Segment—Part 1," *Clin. Cardiol.* 20(6):511-520.

Hurst, J.W. (Jan. 2000). "Methods Used to Interpet the 12-Lead Electrocardiogram: Pattern Memorization Versus the Use of Vector Concepts," *Clin. Cardiol.* 23(1):4-13.

Kors, J.A. et al. (Dec. 1990). "Reconstruction of the Frank Vectorcardiogram from Standard Electrocardiographic Leads: Diagnostic Comparison of Different Methods," *Eur. Heart. J.* 11(12):1083-1092.

Lee, T.H. et al. (2000). "Evaluation of the Patient with Acute Chest Pain," *N. Engl. J. Med.* 342(16):1187-1195.

Levkov, C.L. (Mar. 1987). "Orthogonal Electrocardiogram Derived from the Limb and Chest Electrodes of the Conventional 12-Lead System," *Med. Biol. Eng. Comput.* 25:155-164.

Malik, M. (2004). "Errors and Misconceptions in ECG Measurement Used for the Detection of Drug Induced QT Interval Prolongation," *J. Electrocardiol.* 37(Suppl.):25-33.

Malik, M. et al. (Dec. 2004). "Sample Size, Power Calculations, and Their Implications for the Cost of Thorough Studies of Drug Induced QT Interval Prolongation," *PACE* 27:1659-1669.

McCarthy, B.D. et al. (Mar. 1993). "Missed Diagnoses of Acute Myocardial Infarction in the Emergency Department: Results from a Multicenter Study," *Ann. Emerg. Med.* 22(3)579-582.

McMechan, S.R. et al. (1995). "Body Surface ECG Potential Maps in Acute Myocardial Infarction," *J. Electrocardiol.* 28(Suppl.):184-190.

Mehtha, R.H. et al. (Apr. 20, 2000). "Missed Diagnoses of Acute Coronary Syndromes in the Emergency Room—Continuing Challenges," *N. Engl. J. Med.* 342(16):1207-1210.

Morikawa, J. et al. (Jun. 1987). "Three-Dimensional Vectorcardiography (3-D VCG) by Computer Graphics in Old Myocardial Infarction," *Angiology* 38(6):449-456.

Morikawa, J. et al. (Nov. 1996). "Delineation of Premature P Waves on Four-Dimensional Electrocardiography, a New Display of Electrical Forces by Computer Techniques," *Angiology* 47(11):1101-1106.

Niederberger, M. et al (1977). "A Global Display of the Heart Vector (Spherocardiogram). Applicability of Vector- and Polarcardiographic Infarct Criteria," *J. Electrocardiol.* 10(4):341-346.

Pettersson, J. et al. (1995). "Increased Sensitivity for the Diagnosis of Healed Myocardial Infarction Using Vectorial Information in the 12-Lead ECG," *Journal of Electrocardiology* 28(3):169-175.

Pope, J.H. et al. (2000). "Missed Diagnosis of Acute Cardiac Ischemia in the Emergency Department," *N. Engl. J. Med.* 342(16):1163-1170.

Redz, A. (Mar. 10, 1998). "Presentation and Analysis of Vector Electrocardiograms," located at http://www.nada.kth.se/~anna/masters_thesis.pdf, last visited on Aug. 26, 2008, 38 pages.

Rosamond, W.D. et al. (Sep. 24, 1998). "Trends in the Incidence of Myocardial Infarction and in Mortality Due to Coronary Heart Disease, 1987 to 1994," *N. Engl. J. Med.* 339(13):861-867.

Sada, T. et al. (1982). "Polarcardiographic Study of Inferior Myocardial Infarction: Global Projection of Heart Vector," *J. Electrocardiol.* 15(3):259-264.

Titomir, L.I. et al. (May 1987). "Chronotopocardiography: A New Method of Presentation of Orthogonal Electrocardiograms and Vectorcardiograms," *Int. J. Bio-Medical Computing* 20(4):275-282.

Van Oosterom, A. (1997). "Incorporation of the Spatial Covariance in the Inverse Problem," *Biomedizinische Technik.* 42-E1:33-36.

Yan, G-X. et al. (Nov. 3, 1998). Cellular Basis for the Normal T Wave and the Electrocardiographic Manifestations of the Long-QT Syndrome, *Circulation* 98:1928-1936.

AMPS-QT, The AMPS Quarterly (Mar. 2010), *AmPS Quarterly Magazine*, Issue No. 5, 1Q2010, pp. 1-5.

* cited by examiner

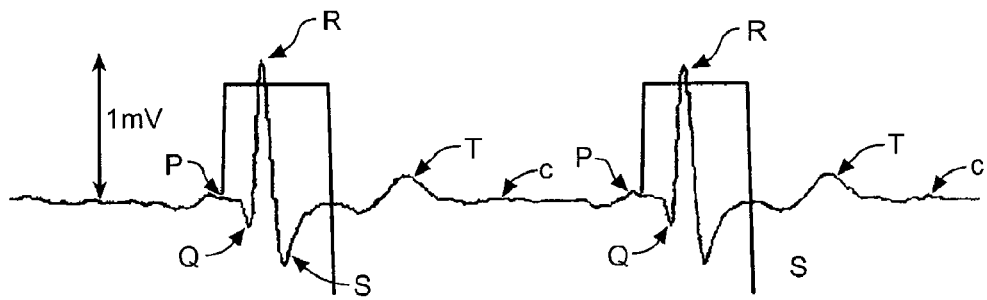

CIF
Basic Functionality CI
=CIFB$_1$ x CIFB$_2$ x CIFB$_3$ x CIFSDQTCT

Where CIFB$_n$ is 0 if it
- fails to meet min voltage criteria,
- fails to fall in an acceptable range of values,
- there is an error message in processing the beat, or
- Tdiff for a beat exceeds 15%

And CIFSDQTCT is
- a value for SD of QTc for the selected triplet that exceeds a user defined threshold

CIT
Triplet Confidence Index
= CITBDMOVE x CITHFACTOR

Where:
- CITBDMOVE = 0, if 1 or 2 bumps detected;
  1 if 0 or 3 detected
- CITHFACTOR = 100 - CITSDQTc - CITSDRR - CITSDTDIFF and components of CITHFACTOR are:
- CITSDQTc increases if std dev for all QTc in triplet exceeds min value (8 msec); rises to 100 if QTc is > 15 ms
- CITSDRR increases if std dev for RRs in triplet exceeds 3 msec, to a max value of 16
- CITSDTDIFF increases if std dev for Tdiff exceeds a 1% threshold, up to a max of 18.

FIG. 16B

CIF
Basic Functionality CI
= $CIFB_1 \times CIFB_2 \times CIFB_3 \times CIFSDQTCT$ Where $CIFB_n$ begins at 1 and is changed as follows with the following conditions:
- Multiply by 0.9 if voltage is 100-120 microV, 0.8 if 85-100 microV, 0.6 if 70-85 uV, and 0 if less than 70 microV,
- Becomes 0 if QTc is <310 msec or >490 msec
- Mult by 0.9 if QTc is 460-475 msec
- Mult by 0.8 if QTc is 475-490 msec,
- Becomes 0 if there is an error message in processing the beat, or
- Becomes 0 if Tdiff for a beat exceeds 15%

And CIFSDQTCT is
- a value for SD of QTc for the selected triplet that exceeds a user defined threshold

FIG. 17A

CIT
Triplet Confidence Index
= CITBDMOVE × CITHFACTOR

Where:
- CITBDMOVE = 0, if 1 or 2 bumps detected;
  1 if 0 or 3 detected
- CITHFACTOR= 100 – CITSDQTc – CITSDRR – CITSDTDIFF – QRS DURATION – J POINT VOLTAGE and components of CITHFACTOR are:
- CITSDQTc increases if std dev for all QTc in triplet exceeds min value (8 msec); rises to 100 if QTc is >15 msec
- CITSDRR increases if std dev for RRs in triplet exceeds 3 msec, to a max value of 16
- CITSDTDIFF increases if std dev for Tdiff exceeds a 1% threshold, up to a max of 18.
- QRS Duration Score is 10 if mean QRS duration is 120 to 140 msec, 25 if 140-150 msec, 40 if 150-160, and 100 if >160.
- J Point Voltage Score is 10 if J Point Voltage is 200-300 uV; 20 if 300-400; 40 if 400-500

User-defined points for high SD of QRS duration in triplet.

FIG. 17B

CIR
Whole ECG Confidence Index
= 100 - all SD components

SD components are:
- SD RR for all RR intervals
- SD Tmax for all Tmax voltages
- SD R, std dev of all Rmax voltages
- SD AA, std dev for all beat areas (RR integral)
- SD QTc, std dev for all QTc in reading
- SD QRS duration, std dev of all QRS durations in reading
- High Heart Rate, reduce CIR score by 20 if mean RR is less than 0.5 sec, by 40 if mean RR is less than 0.4 sec

FIG. 17C

METHOD AND APPARATUS FOR QUANTITATIVE ASSESSMENT OF CARDIAC ELECTRICAL EVENTS

CROSS REFERENCE TO RELATED APPLICATIONS

This application is a divisional of U.S. patent application Ser. No. 12/184,068, filed Jul. 31, 2008, now U.S. Pat. No. 8,209,002, issued on Jun. 6, 2012, which claims benefit under 35 U.S.C. §119 of U.S. Provisional Patent Application Ser. No. 60/963,065, filed Aug. 1, 2007. The foregoing applications are each hereby incorporated by reference into the present application in their entirety.

FIELD OF THE INVENTION

The present invention relates to the field of medical electronics. In particular, it concerns electronic devices for acquisition and presentation of diagnostic data for use with humans or animals.

BACKGROUND

Although the ECG (electro cardiogram) is a universally accepted diagnostic method in cardiology, frequent mistakes are made in interpreting ECGs, because the most common approach for interpretation of ECGs is based on human memorization of waveforms, rather than using vector concepts and basic principles of electrocardiography (see Hurst, J. W., Clin. Cardiol. 2000 Jan.; 23(1):4-13).

Another problem with traditional ECG recordings is that the ECG may not provide adequate indications of electrical activity of certain regions of the heart, especially the posterior region.

The timing of cardiac electrical events, and the time intervals between two or more such events, has diagnostic and clinical importance. However, medical diagnosis and drug development has been significantly limited by the lack of adequate ECG measurement tools.

Furthermore, prior analysis of ECG recordings required a substantial amount of training and familiarity with reading of the recorded waveforms.

There have been many attempts to extract additional information from the standard 12-lead ECG measurement when measuring the electric potential distribution on the surface of the patient's body for diagnostic purposes. These attempts have included new methods of measured signal interpretation, either with or without introducing new measurement points, in addition to the standard 12-lead ECG points.

Vector ECG

VCG is the oldest approach that includes the improvement of a spatial aspect to the ECG (see Frank, E., An Accurate, Clinically Practical System For Spatial Vectorcardiography, Circulation 13: 737, May 1956). Like conventional ECG interpretation, VCG uses a dipole approximation of electrical heart activity. The dipole size and orientation are presented by a vector that continuously changes during the heartbeat cycle. Instead of presenting signal waveforms from the measurement points (waveforms), as it is the case with standard 12-lead ECGs, in VCG, the measurement points are positioned in such a way that three derived signals correspond to three orthogonal axes (X, Y, Z), and these signals are presented as projections of the vector hodograph onto three planes (frontal, sagittal, and horizontal). In this way, VCG represents a step towards spatial presentation of the signal, but the cardiologist's spatial imagination skills were still necessary to interpret the ECG signals, particularly the connection to the heart anatomy. Furthermore, a time-dependence aspect (i.e., the signal waveform) is lost with this procedure, and this aspect is very important for ECG interpretation. VCG introduces useful elements which cannot be found within the standard 12-lead ECG, however, the incomplete spatial presentation and loss of the time-dependence are major reasons why VCG, unlike ECG, has never been widely adopted, despite the fact that (in comparison to ECG) VCG can more often correctly diagnose cardiac problems, such as myocardial infarction.

Modifications of Vector ECG

There have been numerous attempts to overcome the drawbacks of the VCG method described above. These methods exploit the same signals as VCG (X, Y, Z), but their signal presentation is different than the VCG projection of the vector hodograph onto three planes:

"Polarcardiogram" uses Aitoff cartographic projections for the presentation of the three-dimensional vector hodographs (see Sada, T., et al., J. Electrocardiol. 1982; 15(3):259-64). "Spherocardiogram" adds information on the vector amplitude to the Aitoff projections, by drawing circles of variable radius (see Niederberger, M., et al., J. Electrocardiol. 1977; 10(4):341-6). "3D VCG" projects the hodograph onto one plane (see Morikawa, J., et al., Angiology, 1987; 38(6):449-56. "Four-dimensional ECG" is similar to "3D VCG," but differs in that every heartbeat cycle is presented as a separate loop, where the time variable is superimposed on one of the spatial variables (see Morikawa, J., et al., Angiology, 1996; 47:1101-6.). "Chronotopocardiogram" displays a series of heart-activity time maps projected onto a sphere (see Titomir, L. I., et al., Int J Biomed Comput 1987; 20(4):275-82). None of these modifications of VCG been widely accepted in diagnostics, although they have some improvements over VCG.

Electrocardiographic Mapping

Electrocardiographic mapping is based on measuring signals from a number of measurement points on the patient's body. Signals are presented as maps of equipotential lines on the patient's torso (see McMechan, S. R., et al., J. Electrocardiol. 1995; 28 Suppl:184-90). This method provides significant information on the spatial dependence of electrocardiographic signals. The drawback of this method, however, is a prolonged measurement procedure in comparison to ECG, and a loose connection between the body potential map and heart anatomy.

Inverse epicardiac mapping includes different methods, all of which use the same signals for input data as those used in ECG mapping; and they are all based on numerically solving the so-called inverse problem of electrocardiography (see A. van Oosterom, Biomedizinisch Technik., vol. 42-E1, pp. 33-36, 1997). As a result, distributions of the electric potentials on the heart are obtained. These methods have not resulted in useful clinical devices.

Timing of Cardiac Electrical Events

Cardiac electrical activity can be detected at the body surface using an electrocardiograph (ECG), the most common manifestation of which is the standard 12-lead ECG. Typical ECG signals are shown in present FIG. 6. The P-wave 10 represents atrial depolarization. The QRS complex 20 represents depolarization of the ventricles, beginning with QRS onset ($QRS_{on}$) and ending at J point 30. Ventricular repolarization begins during the QRS and extends through the end of the T-wave ($T_{end}$) 70. The ST segment 40 extends from J point 30 to onset of the T-wave 50 ($T_{on}$). T-wave 45 extends from $T_{on}$ 50 to $T_{end}$ 70. U waves (not shown) are present on some ECGs. When present, they merge with the end of the T-wave or immediately follow it.

Physiologically, the T-wave is the ECG manifestation of repolarization gradients, that is, disparities in degree of repolarization at a particular time point between different regions of the heart. It is likely that the T-wave originates primarily from transmural repolarization gradients. (See Yan and Antzelevitch Circulation 1998; 98:1928-1936; Antzelevitch, J. Cardiovasc Electrophysiol 2003; 14:1259-1272.) Apicobasal and anterior-posterior repolarization gradients may also contribute. (See Cohen I S, Giles W R, and Noble D *Nature*. 1976; 262:657-661.)

Transmural repolarization gradients arise because the heart's outer layer (epicardium) repolarizes quickly, the midmyocardium repolarizes slowly, and the inner layer (endocardium) repolarizes in intermediate fashion. Referring to FIG. 6, during ST segment 40, all layers have partially repolarized to a more or less equal extent, and the ST segment is approximately isoelectric. T-wave 45 begins at $T_{on}$ 50 when the epicardial layer moves toward resting potential ahead of the other two layers. At the peak of the T wave ($T_{peak}$) 60, epicardial repolarization is complete and the transmural repolarization gradient is at its maximum. Subsequently, endocardial cells begin their movement towards resting potential, thereby narrowing the transmural gradient and initiating the downslope of the T wave. Finally, the M cells repolarize, accounting for the latter part of the T-wave downslope. The T wave is complete at $T_{end}$ 70 when all layers are at resting potential and the transmural gradient is abolished.

The QT interval may be estimated from an ECG by measuring time from $QRS_{on}$ to $T_{end}$. Abnormalities in the QT interval often mark susceptibility to life-threatening arrhythmias. Such abnormalities may be associated with genetic abnormalities, various acquired cardiac abnormalities, electrolyte abnormalities, and certain prescription and non-prescription drugs.

An increasing number of drugs have been shown to prolong the QT interval and have been implicated as causes of arrhythmia. As a result, drug regulatory agencies are conducting increasingly detailed review of drug-induced abnormalities in cardiac electrical activity. The accuracy and precision of individual measurements is highly important for clinical diagnosis of heart disease and for evaluation of drug safety. Drug regulatory bodies worldwide now require detailed information regarding drug effects on cardiac intervals measured from ECG data. (See M. Malik, PACE 2004; 27:1659-1669; Guidance for Industry: E14 Clinical Evaluation of QT/QTc Interval Prolongation and Proarrhythmic Potential for Non-Antiarrhythmic Drugs, http://www.fda.gov/cder/guidance/6922fn1.pdf). Improved measurement accuracy and precision would reduce the risk of clinical error and the amount of resources required during drug development to meet regulatory requirements.

This is particularly true for QT interval measurement, but also affects determination of virtually all cardiac electrical events, for example onset of the QRS complex ($QRS_{on}$), the J point, onset of the T wave ($T_{on}$), and U waves.

No computerized QT measurement algorithm has demonstrated a sufficient degree of reliability (see M. Malik, J. Electrocardiol 2004; 37: 25-33). Accordingly, the consensus opinion is that QT intervals should be measured manually by experienced observers. (See Anderson M, et al. Am Heart J 2002; 144:769-781.) Unfortunately, manual QT measurement is labor intensive and expensive and remains inherently inaccurate (see Malik et al., Brit Heart J 1994; 71: 386-390).

Problems in manual QT interval determination result in part from lead selection. Measured QT intervals can vary significantly depending upon the ECG lead selected for measurement. Another common problem is finding $T_{end}$. This is usually defined as the point at which the measured voltage returns to the isoelectric baseline. However, T-waves are often low-amplitude, morphologically abnormal, fused with a following U-wave, or obscured by noise. The same may apply to J-points, P-waves, U-waves and other important cardiac events.

Thus, accurate and reproducible procedures for cardiac interval measurement are urgently needed. Also needed are procedures that are rapid and simple, and do not require a high degree of medical training and experience to achieve accurate and reproducible results. Such procedures are needed for QT interval and other critical cardiac electrical events, such as $QRS_{on}$, the J point, J-T interval, $T_{on}$, $T_{on}$-to-$T_{end}$ interval, and the like.

Automated cardiac interval measurement tools have been faced with several issues, including the issue of which lead to use for cardiac interval determination. In response, methods based on an average complex or median complex has been developed. In these approaches, a single representative complex is derived from all available complexes in the ECG under evaluation. The methods for accomplishing vary, however all of them involve some sort of averaging and compensation for different RR intervals and other variations that every ECG typically has. However, these methods are limited by the fact that they do not assess the quality of a complex before it is used in the creation of the average or median complex—for example, overall variability, high-frequency artifacts such as electrical noise or muscle artifact, and low-frequency artifacts such as baseline wander. Thus, a method for selection of an optimal complex or set of complexes based on an objective set of criteria is a significant need for developing a reliable method for automating evaluation of ECGs and determination of cardiac intervals.

SUMMARY

The present disclosure provides accurate, reproducible, and simple methods, systems, and articles of manufacture and apparatus for determining the time of cardiac electrical events and cardiac intervals. This includes devices and procedures for acquisition and analysis of electrocardiographic (ECG) data and the three-dimensional visualization of ECG data that enables more precise diagnostic interpretation of the ECG data and are useful for research and clinical purposes.

Described herein are methods and associated apparatus which are generally computer enabled for determining the time of a cardiac electrical event, comprising providing an ECG "lead" (signal); selecting from the ECG lead a time interval Δt within a cardiac cycle that includes the cardiac electrical event; determining a time-variable heart vector at a plurality of time points within Δt; determining an angular change in the time-variable heart vector between time points t1 and t2 within Δt; wherein the angular change between t1 and t2 is equal to or greater than a specified minimum. In some embodiments, the cardiac electrical event is identified as the pair of time points within Δt between which an angular change in the time-variable heart vector is equal to or greater than the angular change determined for any other pair of time points within Δ. In other embodiments, the ECG lead is a virtual ECG lead, and in yet other embodiments, the angular change in the time variable heart vector is determined using an Angle tool as defined herein. In yet other embodiments, the time-variable heart vector is a normalized time-variable heart vector.

Also described are methods and apparatus for determining the time of a cardiac electrical event using the angle between tangents of the trajectory of the heart vector $\vec{H}$ at at two time points, that is where $\vec{H}=(X,Y,Z)=X\vec{i}+Y\vec{j}+Z\vec{k}$, and the first derivative of $\vec{H}$ is $$\vec{H}_t(t) = \frac{d\vec{H}(t)}{dt},$$

the angle $\gamma$ is:

$$\cos(\gamma) = \frac{\vec{H}_t(t1) \cdot \vec{H}_t(t2)}{|\vec{H}_t(t1) \cdot \vec{H}_t(t2)|},$$

where t1 and t2 are any two time points for which $\vec{H}_t(t)$ is available. These methods comprise providing an ECG lead; selecting from the ECG lead a time interval Δt within a cardiac cycle that includes a cardiac electrical event; determining a time-variable heart vector at a plurality of time points within Δt; determining an angle γ between time points t1 and t2 within Δt; wherein the angle γ between t1 and t2 is equal to or greater than a specified minimum. In some embodiments, the angle γ is equal to or greater than the angle γ determined for any other pair of time points within γt. In other embodiments, the time-variable heart vector is a normalized time-variable heart vector.

The methods and apparatus determine the time of a cardiac electrical event using the difference between the value of K(t) at two time points of interest, t1 and t2, in the cardiac cycle, wherein the second derivative of the heart vector is $$\vec{H}_{tt}(t) = \frac{d^2 \vec{H}(t)}{dt^2},$$

and K(t) at any time point t can be calculated from the formula as explained below:

$$K(t) = \frac{(X_t^2 + Y_t^2 + Z_t^2)(X_{tt}^2 + Y_{tt}^2 + Z_{tt}^2) - (X_t X_{tt} + Y_t Y_{tt} + Z_t Z_{tt})^2}{(X_t^2 + Y_t^2 + Z_t^2)^3}$$

These methods comprise providing an ECG lead; selecting from the ECG lead a time interval Δt within a cardiac cycle that includes a cardiac electrical event; determining a time-variable heart vector at a plurality of time points within Δt; the difference between the value of K(t) between time points t1 and t2 within Δt; wherein the difference in K(t) between t1 and t2 is equal to or greater than a specified minimum. In some embodiments, the difference in K(t) between t1 and t2 is is equal to or greater than the difference in K(t) determined for any other pair of time points within Δt. In other embodiments, the time-variable heart vector is a normalized time-variable heart vector.

Also described are methods for determining the time of a cardiac electrical event, comprising providing a virtual ECG lead; selecting from the ECG lead a time interval Δt that includes a cardiac electrical event; fitting a function with one or more maxima and one or more minima to data points within Δt; identifying the time of a cardiac electrical event a time t1 within Δt which corresponds to a maximum or minimum of the function. In some embodiments, the function is a third-order polynomial function. In other embodiments, the function is fit to the ECG data using least-square fitting techniques, and in yet other embodiments, a reference level for the ECG data may be determined by defining a distribution frequency function F ($x_n$) of voltages within Δt, and setting the reference level equal to the approximate maximum of the distribution frequency function F ($x_n$) within Δt. In still yet other embodiments, the virtual ECG lead may be a $V_{13}$ virtual ECG lead, as the $V_{13}$ virtual ECG lead is defined herein. In some embodiments, a continuous single peak function may be used to approximate F ($x_n$), for example a Gaussian distribution. In still other embodiments, Δt is chosen to include a $QRS_{peak}$ or $T_{peak}$ and an observer marks a fiducial point corresponding to the approximate time of the $QRS_{peak}$ or $T_{peak}$, and in some embodiments, automated means may be used to adjust the observer placement of the fiducial points to a local maximum within Δt that corresponds to the $QRS_{peak}$ or $T_{peak}$.

The methods include determining the time of a cardiac electrical event, comprising providing a virtual ECG lead; selecting from the ECG lead a time interval Δt that includes a cardiac electrical event; fitting a polynomial function with one or more maxima and one or more minima to data points within Δt; identifying the time of a cardiac electrical event a time t1 within Δt which corresponds to a maximum or minimum of a third-order polynomial function, and determining a weighted integral of an absolute difference between the polynomial and the ECG lead within Δt. In some embodiments as explained below, the weighted integral is Tdiff, $$Tdiff[\%] = \frac{\sum_{i=2}^{N-1} |VM(t_i) - VMp(t_i)| + \frac{1}{2}[|(VM(t_1) - VMp(t_1)| + |VM(t_N) - VMp(t_N)|]}{(N-1)|VM(t_1) - VM(t_N)|} 100$$

where VMp(ti) are the values of the third-order polynomial, $VM(t_i)=|\vec{H}(t_i)|$ is the heart vector magnitude and the summation is done in the time interval of interest. In other embodiments, a boundary value for Tdiff may be set, and determinations that exceed the boundary value are identified. The boundary value may be, for example, approximately 1%, 2%, 3%, 4%, 5%, 6%, 8%, 10%, 15%, or more. Other embodiments include, for determinations that exceed the boundary value, selecting from the ECG lead a subset Δt' of Δt that includes fewer time points than Δt and includes the cardiac electrical event; fitting a function with one or more maxima and one or more minima to data points within Δt'; identifying the time of the cardiac electrical event as a time t1' within Δt' which corresponds to a maximum or minimum of the function. Still other embodiments include determining Tdiff within the time interval Δt' identifying determinations of t1' within Δt' wherein the corresponding value for Tdiff exceeds the boundary value; for determinations that exceed the boundary value, selecting from the ECG lead a subset Δt" of Δt' that includes fewer time points than Δt and includes the cardiac electrical event; fitting a function with one or more maxima and one or more minima to data points within Δt"; identifying the time of the cardiac electrical event as a time t1" within Δt" which corresponds to a maximum or minimum of the function.

The methods include determining the time of a cardiac electrical event, comprising providing an ECG lead; selecting in the ECG lead a time interval $\Delta t$ that begins at approximately $QRS_{peak} \times 4*DQ$ and ends at approximately a $QRS_{peak}$; identifying within $\Delta t$ a subset of time points at which the value of HVVM is less than approximately 0.01 mV/sec; selecting as $QRS_{on}$ the time point within the subset that is closest in time to the $QRS_{peak}$. The function HVVM and DQ are as described in detail herein.

The methods include determining the time of a cardiac electrical event, comprising providing an ECG lead; selecting in the ECG lead a time interval $\Delta t$ that begins at approximately $QRS_{peak} - 4*DQ$ and ends at approximately a $QRS_{peak}$; identifying within $\Delta t$ a subset of time points at which the value of VA is less than approximately 0.01 $sec^2/mV^2$; selecting as $QRS_{on}$ the time point within the subset that is closest in time to the $QRS_{peak}$. The function VA is as described in detail herein.

The methods include determining the time of a cardiac electrical event, comprising providing an ECG lead; selecting in the ECG lead a time interval $\Delta t$ that begins at approximately a $QRS_{peak}$ and ends at approximately $QRS_{peak} + 4*DQ$; identifying within $\Delta t$ a subset of time points at which the value of VA (explained below) is less than approximately 0.01 $sec^2/mV^2$; selecting as a J Point the time point within the subset that is closest in time to the $QRS_{peak}$.

The methods include determining the time of a cardiac electrical event, comprising providing an ECG lead; selecting in the ECG lead a time interval $\Delta t$ that begins at approximately a $QRS_{peak}$ and ends at approximately $QRS_{peak} + 4*DQ$; identifying within $\Delta t$ a subset of time points at which the value of HVVM (explained below) is less than approximately 0.01 mV/sec; selecting as a J Point the time point within the subset that is closest in time to the $QRS_{peak}$.

The methods include determining the time of a cardiac electrical event, comprising: providing an ECG lead; selecting a time interval $\Delta t$ that begins at approximately $QRS_{peak} \times 4*DQ$ and ends at approximately a $QRS_{peak}$; identifying within $\Delta t$ a subset of time points within which the magnitude of Heart Vector Acceleration reaches a maximum; selecting as a $QRS_{on}$ a time point within the subset. The term Heart Vector Acceleration is as defined in detail herein.

The methods include determining the time of a cardiac electrical event, comprising providing an ECG lead; selecting in the ECG lead a time interval $\Delta t$ that begins at approximately a $QRS_{peak}$ and ends at approximately $QRS_{peak} + 4*DQ$; identifying within $\Delta t$ a subset of time points at which the magnitude of Heart Vector Acceleration reaches a maximum; selecting as a J Point the time point within the subset that is closest in time to the $QRS_{peak}$.

The present methods and apparatus herein may be used to determine the time of virtually any cardiac electrical event, including but not limited to the beginning and end of the P wave ($P_{on}$ and $P_{end}$, respectively); the beginning, peak, and end of the QRS complex ($QRS_{on}$, $QRS_{peak}$, and J point, respectively); the beginning, peak and end of the T-wave ($T_{on}$, $T_{peak}$, and $T_{end}$, respectively), and the beginning and end of the U wave ($U_{on}$ and $U_{end}$, respectively).

One embodiment simplifies the vector interpretation concept, and provides a visual three-dimensional presentation of a patient's ECG signal with a three-dimensional model of the human heart, rather than relying on the cardiologist's individual spatial imagination skills. The present invention exploits a dipole approximation of electrical heart activity, in keeping with the basis of the conventional doctrine of ECG interpretation.

Another embodiment provides a more accurate approximation of cardiac activity, particularly for regions of the heart, such as the posterior region, that generally were less well represented using prior ECG recordings, and may also provide greater indications of cardiac events such as ischemia.

Another embodiment of this invention provides analysis tools to aid in the interpretation of cardiac electrical activity.

BRIEF DESCRIPTION OF THE DRAWINGS

FIG. 15 shows ECG complexes.

FIGS. 16A, 16B show determination of confidence indices.

FIGS. 17A, 17B, 17C show further determination of confidence indices.

DETAILED DESCRIPTION

Figure 1:
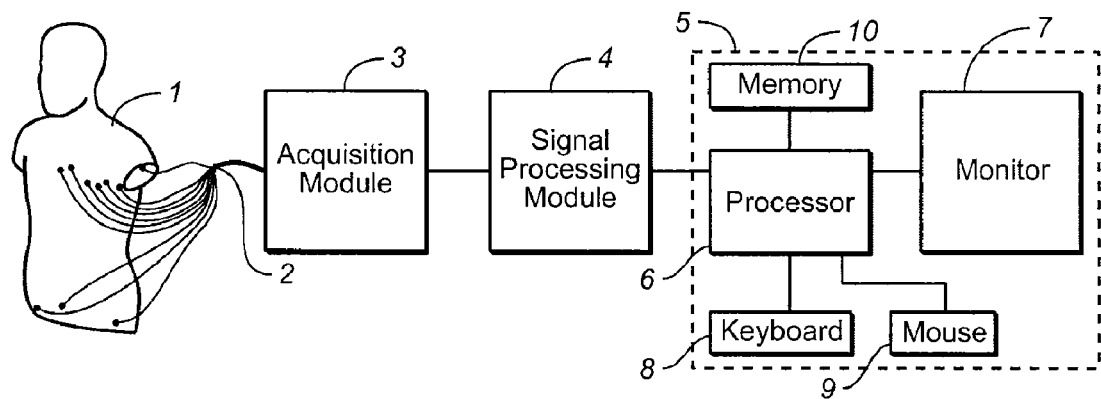
FIG. 1 shows a block diagram of one version of a computer based system or apparatus for three-dimensional presentation of ECG data described herein.

The devices, apparatuses, systems, articles of manufacture, and methods descried herein allow display and analysis of the electrical activity of a heart by processing cardiac ECG data and by providing different types of analytic tools, including computerized three-dimensional spatial presentations of ECG data recorded from a patient. ECG data is provided, processed, and displayed. Data processing and display may be interactively performed by allowing a user to select different data analysis and display parameters. Cardiac electrical signals derived from the provided ECG data may be displayed as a three-dimensional representation on a model heart; this three-dimensional representation may be manipulated by a user, and may be correlated with two-dimensional representations of cardiac electrical signals, such as standard ECG waveforms. Thus, the cardiac electrical signals may be visualized spatially and temporally. Furthermore, cardiac electrical signals may be analyzed with a variety of tools described herein that may simplify or enhance the analysis of cardiac electrical activity. The ECG analyzer described herein may be used to analyze ECG data as described herein.

Acquisition of ECG Data

Any appropriate source of patient ECG data may be used. For example, ECG data may be recorded directly from a patient, or it may be provided from stored, previously recorded data. Thus, the present invention may use real-time ECG data, or ECG data from archived sources.

ECG data may be of any appropriate type. ECG data may be recorded from a plurality of lead sites on the surface of the patient's body. In some versions, standard 12-lead ECG recordings are provided (e.g., leads I, II, III, aVR, aVF, aVL, V1, V2, V3, V4, V5 and V6). Any appropriate number of ECG leads, positioned at any appropriate body sites, may be used. Examples of other ECG lead systems include the "Frank" electrode lead system (e.g., 7 electrodes), the McFee-Parungao Lead System, the SVEC III Lead System, Fischmann-Barber-Weiss Lead System, and the Nelson Lead System. Other examples include addition of right-sided precordial leads, posterior leads, leads placed in higher or lower intercostal spaces, and the like. Although the examples of ECG data described herein refer to the standard 12-lead system, it should be understood that any appropriate ECG lead system may be used without altering the basic principles of the invention. In some versions, information about the source of the ECG data may be provided to the ECG analyzer. For example, the ECG analyzer may adapt the configuration of the display and/or analysis tools based on the source of the ECG data, such as the position of the ECG leads with respect to the heart, the body, and/or to other leads.

Different amounts of ECG data may also be provided. For example, an ECG waveform may contain multiple repeated "PQRST" waveforms. In some versions, multiple cycles of PQRST (e.g., describing multiple heartbeats) may be provided. However, as few as a single PQRST (e.g., a single heartbeat) cycle, or even a portion of one cardiac cycle, may be used. In other versions, signal-averaged ECG waveforms (Signal-Averaged Electrocardiography: Expert Consensus Document, J Am Coll Cardiol 1996; 27: 238-49) may be used.

Additional patient data may also be provided, including patient statistics (height, weight, age, etc.), vital signs, medical history, physical exam findings (for example, extra heart sounds, rubs, or murmurs) and the like. Such patient data may be used in conjunction with patient-specific ECG data for data processing and display, or it may be used to correlate information extracted from the ECG data. For example, the orientation of the heart may be calculated based on patient-specific data (e.g., height, weight, torso circumference, etc.) and may be used to orient the heart model and other analytic features.

ECG Analyzer

Data may be acquired by the ECG analyzer or it may be obtained from another source (e.g., an ECG recorder, etc.). As used herein, "obtaining ECG data" refers to any appropriate method of obtaining or receiving ECG data, including, but not limited to, directly measuring ECG data, reading ECG data from a recorded (e.g., archived) source, and receiving ECG data from another device. In some versions, the ECG analyzer comprises an acquisition module. An acquisition module may "condition" (or "precondition") data that it receives. For example, an acquisition module may filter, amplify, format, or otherwise operate on ECG data provided from any source, including stored data sources. The ECG analyzer may also receive non-ECG data, including patient data. In some versions, an acquisition module acquires ECG data by direct input from electrical leads connected to a patient.

Signal Processing

Patient ECG data may be processed and displayed. Analysis and visualization of the electrical activity of the heart may be simplified by approximating the electrical activity of the heart as an electric dipole. Thus, ECG data may be transformed into a heart vector representing the electrical phenomena in the heart. A heart vector may be defined by three orthogonal projections: X, Y, and Z. If the provided ECG data is not in the form of a heart vector, then the recorded ECG data (actual ECG data) may be used to compute a heart vector (e.g., from a standard 12-lead ECG). The heart vector may be used with a lead vector (approximating tissue attenuation) to calculate "virtual" ECG waveforms. Furthermore, the heart vector may be normalized by a normalization factor so that the resulting normalized heart vector, and any virtual ECG waveforms calculated from the normalized heart vector, may be used to accurately and precisely analyze the cardiac electrical activity of the heart.

Computation of the Heart Vector

ECG data provides a time-dependent voltage that reflects the electrical activity of the heart over time; multiple ECG lead sites provide different time-dependent voltage waveforms that reflect this overall electrical activity. Given the spatial location of the ECG leads, a single time-dependent heart vector may be computed by approximating the heart electrical activity as a dipole having an origin near the center of the patient's heart. A time-dependent heart vector that represents the size and orientation of the time-varying electrical dipole may be calculated by approximating the electrical activity of the heart.

As few as three leads (corresponding to four to six electrodes) may be used to obtain the X, Y, Z orthogonals of the heart vector. Given a set of leads, any appropriate matrix may be used to convert them to the X, Y, Z orthogonal components of the heart vector. For example, a heart vector may be calculated from standard 12-lead ECG data by transforming the 12-leads into X,Y,Z (e.g., Frank) leads. In one version, a conversion matrix may be used to transform the 12-lead ECG voltages into the three orthogonal components, X,Y, and Z. When converting 12-lead ECG data into a heart vector, an inverse Dower matrix may be used. Examples of the Dower matrix and the inverse Dower matrix may be found in U.S. Pat. Nos. 4,850,370 and 5,711,304, which are herein incorporated by reference in their entirety. Other types of matrices may be used to transform the ECG data (e.g., 12 lead ECG data) into a heart vector, such as a Levkov matrix (Levkov, C.L., Orthogonal electrocardiogram derived from the limb and chest electrodes of the conventional 12-lead system, Med. Biol. Eng. Comput. 1987, 25, 155-164). Any appropriate means may be used to convert the ECG data into the heart vector. In some versions, a matrix or conversion paradigm could be derived, e.g., from experimental data. As used herein, unless the context makes it clear otherwise, a matrix is a set of linear equations that define a transformation between two sets of variables.

The heart vector is a dipole representation of the cardiac electrical signal of the heart, and may be calculated from recordings taken at some distance from the surface of the heart (e.g., from body surface electrodes, internal electrodes such as esophageal electrodes, and combinations of internal and external electrodes).

EXAMPLE 1

Calculation of a Heart Vector From Actual ECG Data

For example, a heart vector may be calculated from 8 standard ECG leads (recorded at leads I, II, $V_1$, $V_2$, $V_3$, $V_4$, $V_5$, and $V_6$). In this example, an Inverse Dower matrix is used to convert the data from the standard leads into the time variable heart vector that represents the size and orientation of a time varying electrical dipole approximating the electrical current (and voltage) of the heart.

The heart vector is described by $\vec{H}$:

$$\vec{H} = (X, Y, Z) = X\vec{i} + Y\vec{j} + Z\vec{k} \qquad (1)$$

The ECG data from eight independent ECG leads can be described as a vector, $\vec{V}$:

$$\vec{V} = (I, II, V_1, V_2, V_3, V_4, V_5, V_6) \qquad (2)$$

leads I, II, $V_1$, $V_2$, $V_3$, $V_4$, $V_5$, and $V_6$ described the recorded potentials from the ECG recorded at the actual lead sites on the surface of a patient's body.

Using an Inverse Dower matrix (ID), the ECG data may be converted into the heart vector containing three orthogonal components, X, Y, Z. In this case, a reasonable inverse Dower matrix is given by:

$$ID = \begin{vmatrix} .156 & -.00893 & -.173 & -.0747 & .122 & .231 & .239 & .194 \\ -.223 & .875 & .056 & -.018 & -.104 & -.0209 & .0408 & .0476 \\ .0225 & .101 & -.229 & -.310 & -.246 & -.0626 & .0550 & .109 \end{vmatrix} \qquad (3)$$

This inverse Dower matrix (3×8) may be applied to ECG signals recorded from the standard positions of the leads (see Pettersson et al., *J. Cardiol.* 28:169, 1995). From equations (2) and (3), the heart vector may be calculated by matrix multiplication:

$$\vec{H} = ID \cdot \vec{V} \qquad (4)$$

which is equivalent (expressed as linear equations) to:

$$X = 0.156 \cdot I - 0.00893 \cdot II - 0.173 \cdot V_1 - 0.0747 \cdot V_2 + 0.122 \cdot V_3 + 0.231 \cdot V_4 + 0.239 \cdot V_5 + 0.194 V_6 \qquad (5)$$

$$Y = -0.223 \cdot I + 0.875 \cdot II + 0.056 \cdot V_1 - 0.018 \cdot V_2 - 0.104 \cdot V_3 - 0.209 \cdot V_4 + 0.0408 \cdot V_5 + 0.0476 \cdot V_6 \qquad (6)$$

$$Z = 0.225 \cdot I + 0.101 \cdot II - 0.229 \cdot V_1 - 0.310 \cdot V_2 - 0.246 \cdot V_3 - 0.0626 \cdot V_4 + 0.0550 \cdot V_5 + 0.109 \cdot V_6 \qquad (7)$$

Thus, the X, Y, and Z components of the heart vector may be solved at any time point by applying the ECG data into these linear equations.

The dipole approximation of heart activity given by the heart vector offers an approximation of cardiac electrical activity, however the heart vector does not give the electrical activity at any particular body surface. For example, the cardiac electrical signals present in an ECG waveform are typically recorded from the surface of the body (or from some internal body sites some distance from the heart). Thus, electrical activity arising from the heart is attenuated by body tissues between the heart and the point of measurement. An empirically determined "lead vector" may therefore be used to estimate a "virtual" signal waveform (e.g., an ECG waveform) recorded anywhere around the heart.

Computation of Signal Waveforms at an Arbitrary Point From a Model Heart

In general, a heart vector and a lead vector may be used to derive an ECG signal waveform at any position around the heart. A lead vector, L, may be described by components $1_x$, $1_y$, and $1_z$. The magnitude of a lead vector describes the attenuation factor of body tissue between the source of the electrical phenomenon (the heart) and a "virtual" recording position (see H. E. Burger, J. B. van Milaan, Heart Vector and Leads, Brit. Heart J. 10:229, 1948). For example, a lead vector describing the attenuation factors from the heart to points on the body surface may have magnitudes of different values corresponding to different attenuation factors (i.e. distances from the heart center). Thus, any appropriate lead vector may be used to derive virtual ECG recordings. In some versions, the lead vector may be determined based on empirical measurements. As used herein, unless the context makes clear otherwise, the term "lead vector" may refer to both a real electrode measurement (when the parameters of the electrode reflect the direction and attenuation of the signal at the measurement point), and a parameter of a virtual (or imaginary) measurement surface, defined by a direction and an attenuation factor for a point on the virtual surface.

The lead vector may have a direction corresponding to the position of the recording electrode (e.g., an actual recording electrode or a "virtual" recording electrode) on the body surface, and a magnitude approximately equal to some attenuation factor similar to the electrical attenuation between the heart and the surface of the body where the recording electrode would lie. Thus, by scalar multiplication, a cardiac electrical signal (e.g., an ECG waveform) may be determined for any virtual lead, and any position around the heart may be chosen as a virtual lead. For example, a point (virtual lead) may be selected from the surface of a heart model that is centered using the same coordinate origin as the heart vector and the lead vector. Any point around the heart model may be correlated to a lead vector having a direction including that point (e.g., $1_x$, $1_y$, and $1_z$ where (x, y, z) are the Cartesian coordinates of the point). Thus, an arbitrary point selected from the heart model may generate a virtual ECG by scalar multiplication of the time-dependent heart vector and the lead vector having the spatial direction of that point.

The scalar product of the lead vector at that point and the heart vector gives the instantaneous potential of the ECG lead for that electrode position. This relationship may be represented by:

$$v_L = \vec{H}(t) \cdot \vec{L} = l_x \cdot X + l_y \cdot Y + l_z \cdot Z \qquad (8)$$

Where $V_L$ is the time-dependent electric potential at an arbitrary point on the patient's body (the value of the recorded lead signal), $1_x$, $1_y$, $1_z$ are the components of the lead vector $\vec{L}$ from that arbitrary point on the body surface, and X, Y, and Z are the components of the heart vector, i.e., the values in three orthogonal vector leads as they have been defined previously.

Thus, a virtual ECG waveform calculated for a point on a body surface around the heart may be approximated by the scalar product of the heart vector and an attenuation factor (given by a lead vector) at that point.

Both the virtual (simulated) and actual (recorded) ECG waveforms reflect the voltage arising from the heart that is recorded at some point on the body surface. This electrical signal has passed from the heart, through the body tissue, and been attenuated depending upon where on the body surface the ECG waveform is recorded. Thus, it is difficult to accurately compare the magnitudes of electrical signals recorded (or simulated) at different points on the surface of the body to each other, or to an empirical electrical criterion (e.g., ST depression or elevation) useful for analyzing the heart. Furthermore, the magnitudes of derived heart vectors (e.g., Frank vectors) are typically undefined, and correspond only to an imaginary surface centered around the heart. However, the heart vector may be normalized such that the voltage (or current) from ECG waveforms simulated anywhere around the heart may be reliably compared with clinically relevant benchmarks.

Normalization of the Heart Vector

The heart vector may be normalized by any appropriate method allowing comparison of the normalized heart vector (or cardiac electrical signals derived from the normalized heart vector) to a clinically relevant benchmark. For example, the heart vector may be normalized by scaling the magnitude of the heart vector over all time by a normalization factor. The normalization factor may be derived from actual ECG data specific to each patient. The normalization factor may define a normalization surface (e.g., a sphere) which is centered at the origin of the heart vector. As used herein, the term "scaling" includes multiplying a vector a normalization factor so that the magnitude of the vector is multiplied by the normalization factor.

In general, the normalization factor is determined by minimizing the difference between actual and virtual voltages recorded at selected leads. Normalization only changes the magnitude (not the direction) of the heart vector.

The heart vector may be normalized so that the magnitude of the heart vector (or virtual ECG waveforms derived from the normalized heart vector) may be comparable to the magnitude of signals recorded from individual precordial leads or any combination of precordial leads. The precordial leads (e.g., leads $V_1, V_2, V_3, V_4, V_5, V_6$) are well characterized, and a number of clinically relevant benchmarks for cardiac phenomena have been derived from the magnitude of regions of ECG waveforms recorded from standard precordial sites (e.g., ST elevation/depression, R-wave magnitude, and the like). Thus, the leads chosen for normalization should correspond to leads whose recorded signals contribute to the establishment of the particular benchmark (or criterion) that will be used to analyze the virtual heart vector. Thus, although any lead may be used to normalize the heart vector (including non-precordial leads, such as the limb leads), leads that did not correspond to the establishment of the particular benchmark may negatively impact the normalization, and should not be included in normalization for that particular benchmark or criterion.

In one version, a normalization factor ($\rho$) is derived by first calculating an individual normalization lead factor ($\rho_i$) for each actual lead, i. Thus, if the six precordial leads are used to determine the normalization factor, an individual lead normalization factor ($\rho_i$) is calculated for each of the six precordial leads ($V_i$, where i=1 to 6), and the normalization factor $\rho$ is selected from the range defined by the maximum and minimum value of these six lead normalization factors.

In this example, each lead normalization factor ($\rho_i$) is calculated by solving for the minimum value of the least-squares difference between the actual ECG waveform over some time (T) and a virtual ECG waveform calculated from the heart vector at that point (by scalar multiplication to a lead vector, as described above), over the same time (T). In some versions, each lead normalization factor ($\rho_i$) is approximately equal to a value that sets the magnitude of a virtual ECG waveform generated using the scaled heart vector to approximately the same magnitude as the actual ECG waveform recorded at the same position around the heart (e.g., the same lead position). The normalization factor ($\rho$) is then selected from within the range of the individually calculated lead normalization factors ($\rho_i$).

Put another way, each lead normalization factor is approximately equal to the ratio (e.g., the least-squares difference) between a cardiac signal derived from the heart vector for a given lead over some time period (e.g., a "virtual" ECG signal recorded at a lead for 5 seconds), and an actual cardiac signal recorded at the same lead for the same time period of time. Thus, a lead normalization factor may be chosen so that error between the recorded and derived leads is minimized. In some versions, the normalization factor is chosen so that difference between the actual and derived leads recorded nearest the chest (e.g., the precordial leads) is minimized. Normalization factors calculated using the precordial leads are appropriate when using an analysis criterion based on a clinically relevant benchmark (e.g., voltage or current) measured for precordial electrodes or electrodes with comparable signals.

Thus, when calculating the normalization factor, a "virtual" signal waveform may be calculated from the heart vector at the position of an actual lead, as described in more detail above.

EXAMPLE 2

Calculation of a Normalization Factor

In this example, a normalization factor ($\rho$) is calculated using six standard precordial leads. $V_i(t)$ is the recorded voltage over time from a lead (e.g., the actual voltage from precordial leads 1 to 6, where i=1 to 6), and $Vd_i(t)$ is the derived voltage for each of the ECG leads (e.g., the same leads 1 to 6). As previously described, virtual lead voltages are calculated as a scalar product of the heart vector $\vec{H}$ and a lead vector, $\vec{L}_i$, with equation (8) or equivalently, $$Vd_i(t) = \vec{H}(t) \cdot \vec{L}_{0i} \cdot \rho_i, \qquad (9)$$

where $\vec{L}_{0i}$ is the unit vector defined having the direction of the position of the i-th electrode (e.g., precordial electrode 1 to 6), and $\rho_i$ is an unknown normalization factor for each electrode. When normalizing the heart vector, the derived voltage is set approximately equal to the actual voltage recorded at the same lead:

$$Vd_i(t) \approx V_i(t) \qquad (10)$$

The unknown factor $\rho_i$ for every lead can therefore be calculated as a minimum of the function:

$$F_i = \int_0^T \left[ V_i(t) - \vec{H}(t) \cdot \vec{L}_{0i} \cdot \rho_i \right]^2 dt \qquad (11)$$

where T is the recording time (e.g., 5 seconds). From this, we derive the relationship:

$$\rho_i = \frac{\int_0^T V_i(t) \cdot [\vec{H}(t) \cdot \vec{L}_{0i}] dt}{\int_0^T [\vec{H}(t) \cdot \vec{L}_{0i}]^2 dt} \quad (12)$$

Thus, we can calculate the lead normalization factors corresponding to each of the precordial electrodes (i=1 to 6). From all of these normalization factors, we can determine a common normalization factor, $\rho$. For example, the common normalization factor may be the average value of the individual normalization factors (e.g., when recorded from the six precordial leads):

$$\rho = \frac{\sum_{i=1}^{6} \rho_i}{6}. \quad (13)$$

Although equation (13) illustrates the normalization factor as an average of individual lead normalization factors, a normalization factor may be any value from the range defined by the lead normalization factors (e.g., the range defined by the maximum and minimum lead normalization factors). Furthermore, a normalization factor ($\rho$) for the heart vector may be any reasonable combination of lead normalization factors. For example, the normalization factor may be equal to the median of a plurality of lead normalization factors. Although example 2 shows the calculation of a normalization factor ($\rho$) from six precordial leads, a normalization factor may be calculated using only a single lead (e.g., $V_1$) or any combinations of leads (e.g., $V_2, V_3, V_4$), including non-standard leads. In particular, the normalization factor may be calculated using the leads (e.g., actual leads) comparable to leads used to derive (or used with) any criterion or benchmark applied by the ECG analyzer.

Furthermore, it should be apparent that the calculation of $\rho$ does not require the calculation of individual lead normalization factors, $\rho_i$. For example, a normalization factor may be calculated from the least-squares difference of the sums of the actual lead waveforms and the virtual lead waveforms, over some time, T.

The heart vector may be normalized by scaling the magnitude of the heart vector with the normalization factor, $\rho$:

$$\vec{H}_{NORMALIZED}(t) = \vec{H}(t) \cdot \rho \text{ or} \quad (14)$$

$$\vec{H}_{NORMALIZED}(t) = \rho(X\vec{i} + Y\vec{j} + Z\vec{k}) \quad (15)$$

where $\vec{H}_{NORMALIZED}(t)$ is the normalized heart vector. From the normalized heart vector, a normalized "virtual" ECG waveform can be calculated at an arbitrary point around the heart, as previously described:

$$V'_L = \vec{H}_N(t) \cdot$$
$$\vec{L}_0 = X_N \cdot l_{0x} + Y_N \cdot l_{0y} + Z_N \cdot l_{0z} = \rho(X \cdot l_{0x} + Y \cdot l_{0y} + Z_N \cdot l_{0z}) \quad (16)$$

where $V'_L$ is the normalized time-dependent electric potential at an arbitrary point on the patient's body, and $(l_{0x}, l_{0y}, l_{0z})$ are the components of the $\vec{L}_0$ with the direction of a lead vector $\vec{L}$ for that arbitrary point on the body surface, and (X, Y, Z) are the orthogonal components of the heart vector, and $(X_N, Y_N, Z_N)$ are the orthogonal components of the normalized heart vector and $\rho$ is the normalization factor.

Normalization may allow comparison of cardiac voltage levels anywhere around the heart with clinical benchmarks (e.g., ST-segment shift), or with other regions of the heart. Normalization may be particularly helpful for ECG or other tests that rely, at least in part, on the magnitude of recorded cardiac electrical signals, such as ST segment shift, which is one of the most widely accepted diagnostic tests for ischemia.

While heart vectors may be able to provide information about cardiac electrical activity anywhere around the heart (e.g., away from the recording electrodes), and may be used to generate "virtual" ECG tracings, the magnitudes of these signals may not be adequately analyzed unless they are normalized as described herein. Normalizing the heart vector, and therefore any "virtual" ECG tracings generated from the normalized heart vector, may allow the magnitude of the cardiac electrical data from any virtual recording location around the heart to be compared with clinically proven criterion.

A normalization factor may be calculated for each individual patient ECG data set. Normalization factors may therefore be patient specific or patient ECG-data set specific. Preliminary results suggest that normalization factors calculated using the six precordial leads may be highly variable between patients, emphasizing the importance of normalizing for each set of patient data, so that the same criterion may be used to analyze patient heart data across patient populations.

Any of these cardiac electrical signals (e.g., heart vectors, normalized heart vectors, etc.) may be presented with a three-dimensional model of the heart that contains both temporal and spatial information about cardiac electrical activity, and may be coordinated with traditional ECG waveforms or the simulated and/or normalized signal waveforms. This displayed information may allow manipulation and further analysis of the cardiac electrical data.

Display of Cardiac Electrical Activity

Recorded and simulated cardiac data may be displayed and manipulated by the user in three-dimensional and two-dimensional representations. Cardiac electrical signals may be represented on a three-dimensional model of a heart; this model may be rotated by the user or automatically rotated. A user may select points on the heart for which cardiac electrical signals may be displayed. One or more ECG waveforms may also be displayed along with the three-dimensional model of the heart, e.g., as a two-dimensional plot of voltage over time.

Heart Model

Any suitable model of the heart (e.g., anatomical models) may be used as the heart model, including simulated heart models, and heart models based on actual patient data. In some versions, the heart model may be correlated to actual patient physiology. For example, the heart model may be derived from a medical scanning technique (e.g., CT, MRI, etc.) Thus, the heart model may reflect individual patient anatomy.

In some versions, the heart model may be entirely simulated. Such models may be based on actual patient data (e.g., a composite based on population information). A variety of heart models may be used. For example, classes or categories of heart models may be used that reflect a population that may be matched to the patient whose ECG data is being analyzed. For example, the ECG analyzer may choose which heart model to use based on information provided about the patient, including characteristics from the ECG data and additional information. Thus, there may be typical heart models for gender, weight, age, etc.

The heart model may also be a combination of patient data and simulation. The heart model may include features that reflect an individual patient's anatomy, medical condition, or medical history. For example, the heart model may be a simulated heart that contains markers indicating previous coronary events, scars, or surgical operations.

Presentation of Cardiac Data

FIG. 1 shows one example of a device for providing a three-dimensional presentation of ECG data. A patient 1 is connected to the conventional ECG electrodes and cables 2 for recording standard 12-lead ECG (leads I, II, III, aVR, aVF, aVL, V1, V2, V3, V4, V5 and V6). Data may be acquired by a conventional acquisition module 3 that amplifies and A/D (analog/digital) converts the electrical signal. It may contain an amplifier level and an A/D converter. Thus, an acquisition module may function as a standard digital ECG device.

Figure 2:
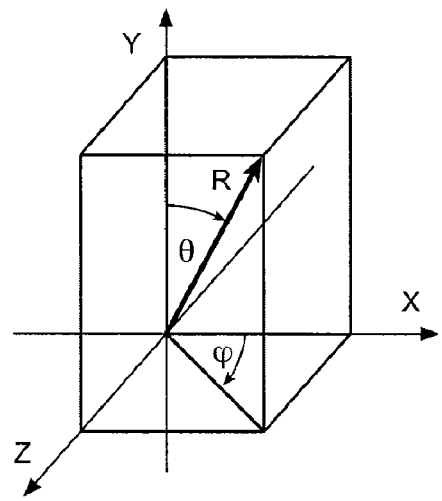
FIG. 2 shows the Frank orthogonal coordinate system.

In this example, conventional signal processing module 4 filters, eliminates the base line fluctuation, and converts the standard 12 ECG leads into three orthogonal vector leads X, Y and Z. (The terms "leads" or "lead" here also refer to signals.) Frank vector leads are used for the derived X, Y, and Z leads, as described (see Frank, E., An Accurate, Clinically Practical System For Spatial Vectorcardiography, *Circulation* 13: 737, May 1956). An orthogonal coordinate system with the axis orientation used for the Frank vector system is shown in FIG. 2. An inverse Dower's matrix is used for conversion of 12 leads into X, Y, and Z (see Edenbrandt, L., Pahlm, 0., Vectorcardiogram synthesized from a 12-lead ECG: superiority of the inverse Dower matrix, *J. Electrocardiol.* 1988 Nov.; 21(4):361-7). The three orthogonal leads X, Y, and Z may be obtained by other conversion matrices or other methods. For example, Kors (see Kors, J. A. et al., Reconstruction of the Frank vectorcardiogram from standard electrocardiographic leads: diagnostic comparison of different methods, *Eur. Heart J.* 1990 Dec.; 11(12): 1083-92), Levkov (see Levkov, C. L., Orthogonal electrocardiogram derived from the limb and chest electrodes of the conventional 12-lead system, *Med. Biol. Eng. Comput.* 1987, 25, 155-164), and the like.

In this example, an interactive visualization module 5 in FIG. 1 includes a conventional computer or computing device with a processor 6, a monitor 7, input and output devices (a keyboard 8 and a mouse 9), and memory 10. The visualization module accepts signals X, Y, and Z from the signal processing module 4, enabling different ways of visualizing the electrical activity of the heart on the monitor screen 7. Recorded signals, including personal and other diagnostic data of a patient, may be stored in digital form in conventional databases in the memory 10 or used in data processing or display. The software executed by the FIG. 1 system includes the functionality disclosed here, and the software by itself in that sense is an apparatus.

Figure 3:
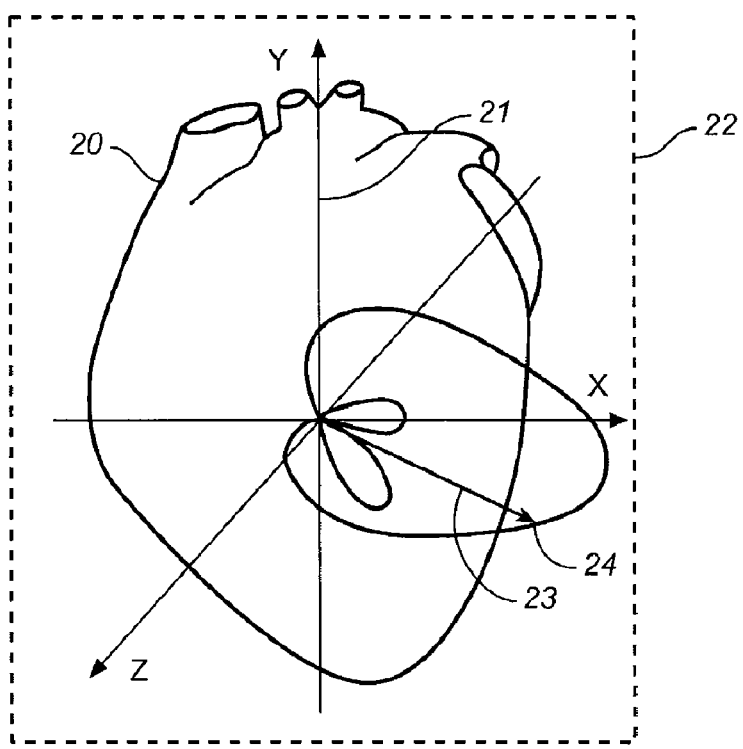
FIG. 3 shows a heart vector hodograph on a three-dimensional heart model.
Figure 4:
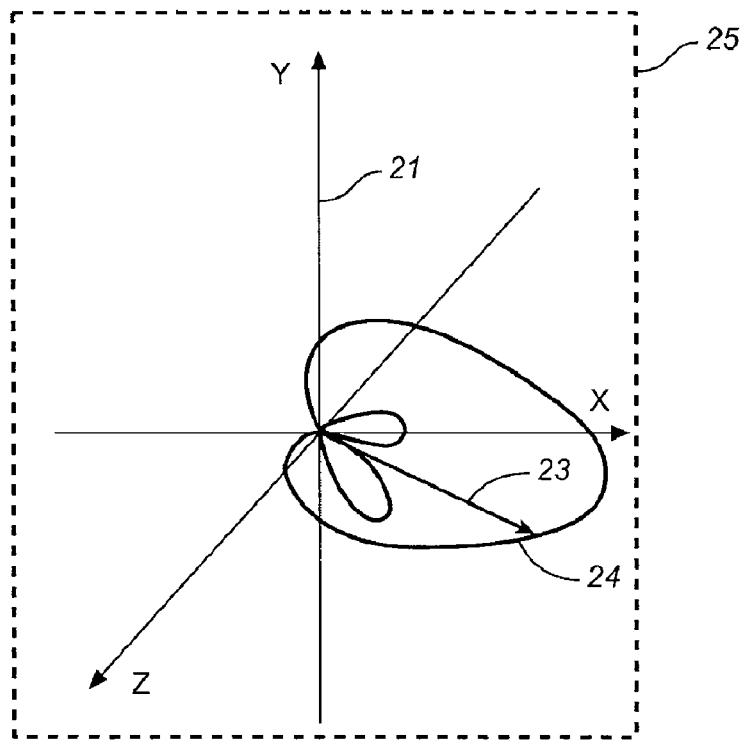
FIG. 4 shows an isolated hodograph of a heart vector.
Figure 5:
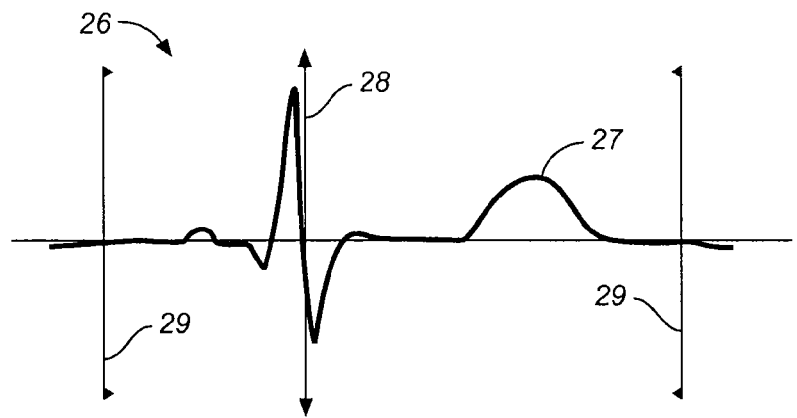
FIG. 5 shows an example of a waveform from one of 12 standard ECG leads.
Figure 6:
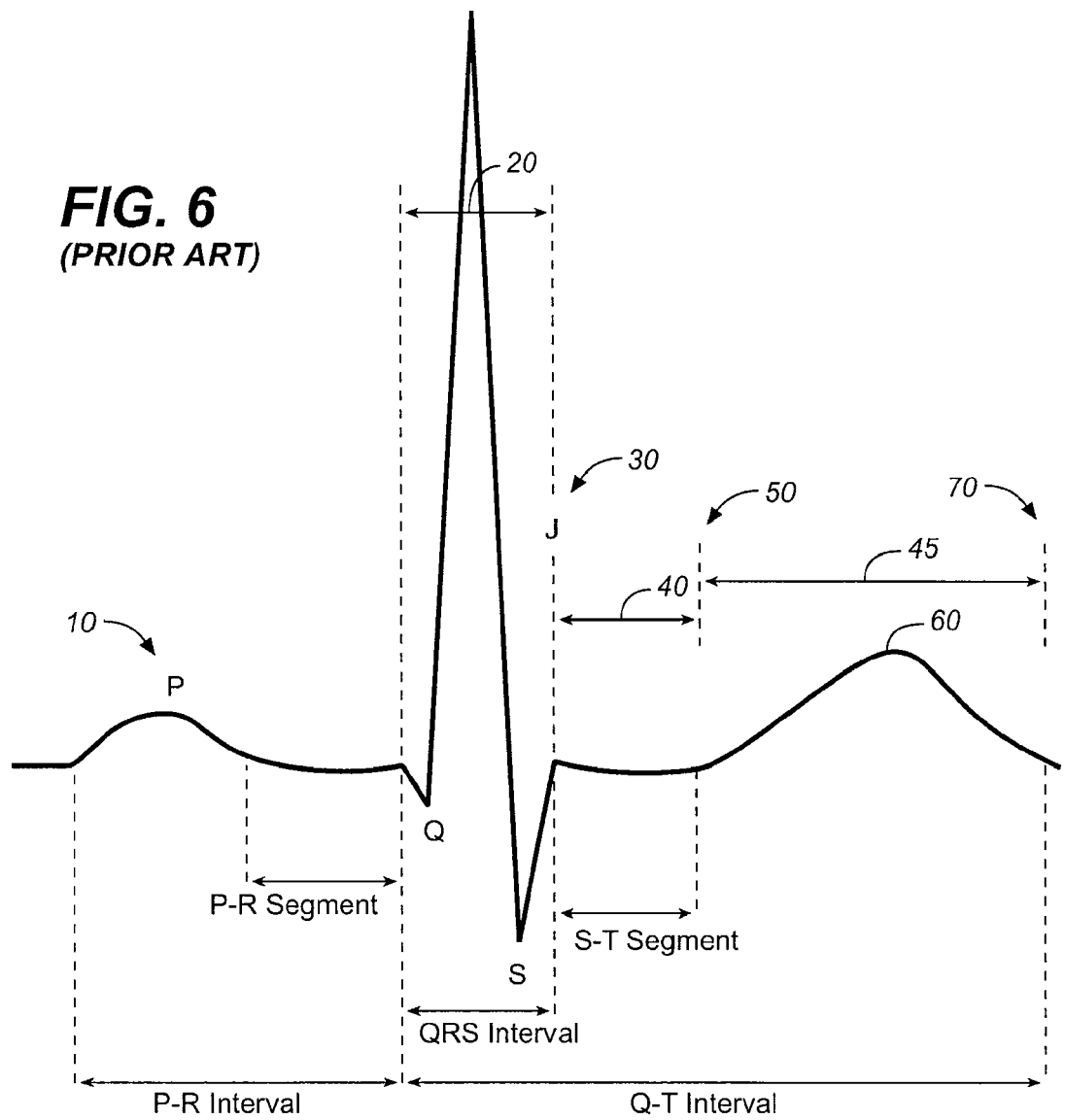
FIG. 6 shows an ECG waveform with cardiac electrical events and time intervals noted.

The basic assumption enabling visualization of the electrical activity of the heart is that electrical activity can be approximated by an electric dipole. The electrical signal of the heart may be presented on a three-dimensional model of the heart 20, as shown in FIGS. 3, 4, and 5. The heart model can include basic anatomic elements, such as the aorta and other major blood vessels. Input and output devices (e.g., the keyboard 8 and the mouse 9) may be used conventionally for interactive manipulation of the model 20 and of the presented signals.

The model may be rotated. For example, the model may be interactively rotated around two orthogonal rotation axes (e.g., using the mouse 9), and it may be brought into any position on screen, meaning that any view of the heart and associated signal can be chosen by a user. The heart model may be rotated around two imaginary rotation axes (which may not be shown on screen), such as the horizontal and vertical axes in the screen plane. A user may control the movement of the heart model through any appropriate input device (e.g., a keyboard or mouse). For example, by moving a mouse 9, the model may be rotated up-down and left-right. In some versions, the model heart is rotated automatically (e.g., it may center a particular feature such as electrical potential or cardiac abnormality, or it may continuously rotate about one or more axes).

As the model is rotated, any information displayed on the heart model may also be rotated. For example, the coordinate system for the model, the heart vector, and the lead vector may be rotated with the heart model. The coordinate system 21 is linked to the model, and may be shown as three orthogonal axes X, Y, and Z, which are rotated together with the rotation of the heart model, so that the model orientation regarding the patient's body is obvious at any view angle. An orientation guide, or body-referenced coordinate system, may also be included for indicating the orientation of the heart relative to a patient. For example, a small figure of a person may be displayed and oriented to show the heart orientation relative to a patient's body.

The heart model (or portions of the model) can be made transparent. For example, a user may select a command from the keyboard 8 or the mouse 9 to make a portion of the model transparent, revealing basic anatomic structures within the heart (e.g., atria and ventricles).

Visualization of analyzed ECG data may include: (1) graphical presentation of the heart vector hodograph, (2) graphical presentation of the signal waveform at an arbitrarily chosen point on the heart, and (3) graphical presentation of the map of equipotential lines on the heart at a chosen moment.

Graphical Presentation of the Heart Vector Hodograph

Graphical presentation of the heart vector, and the heart vector hodograph, is shown in FIGS. 3, 4, and 5. When the heart vector hodograph is shown on screen, three elements may be visible: the first element 22 (FIG. 3) shows the heart vector 23 and its hodograph 24 on a three-dimensional heart model 20, i.e., it shows the path line of the top of the heart vector during a single heartbeat cycle; the second element 25 (FIG. 4) shows the hodograph 24 of the heart vector with the heart vector 23 and coordinate system 21 without displaying the heart model; the third element 26 (FIG. 5) gives a waveform 27 of one of the 12 standard ECG leads. The waveform may be selected from either an actual ECG waveform (e.g., from the data presented) or it may be a virtual waveform selected using the heart model. Waveforms from any of the 12 standard ECG leads, which may be presented as in element 26, may be chosen interactively. The heart model may also indicate the location of the lead from which the ECG waveform originated.

These three display elements may be correlated so that when a time or spatial point is selected from one display, the selection (or change) is reflected in the other displays. In FIGS. 3 and 4, the heart vector is shown by the arrow 23 at the same moment in time. The moment (e.g., the time value for this heart vector) is correlated to the position of the vertical marker line 28 in the ECG waveform in FIG. 5 (element 26). A user can select any time value. In some versions, the user may select a time value by interactively moving (or placing) a cursor 28 on an ECG waveform. In this way, a major drawback of vector ECG related to the loss of the time axis, i.e., the waveform, as mentioned earlier has been eliminated.

The user may also select the time interval to be displayed on the heart vector hodograph (e.g., the number of heart cycles or amount of a single heart cycle). In FIG. 5, element 26, showing the waveform, there are two vertical marker lines 29 (left and right) that can be moved interactively along the waveform, thus defining a time interval (between the two marker lines) shorter that a complete heartbeat cycle, making only the corresponding portion of hodograph visible. In FIG. 5, the brackets 29 show that a complete cardiac cycle (PQRST) have been selected, and are displayed as a cardiac hodograph in FIGS. 3 and 4. In some versions, the user selects the time period of interest. For example, the user may interactively move the brackets 29. When multiple cycles are selected, the hodograph may be computed by processing the data from different cycles so that a single (e.g., averaged or subtracted) hodograph is shown.

The heart model and visualized electrical activity may be moved interactively, and rotation of the different components (e.g., the 3D and 2D elements) may be synchronized. For example, the common axes of the coordinate systems 21 may be kept parallel at any view angle. The same applies to the presentation of the heart vector 23 in the elements 22 and 25.

Graphical Presentation of the Signal Waveform for an Arbitrarily Chosen Lead on the Heart A "virtual" lead may be calculated using the normalized heart vector for any point on the surface of a heart model. The point may be selected by the user. In some versions, the user may select any point on the continuous surface of the heart model. In some versions, regions of the heart model may not be selectable (e.g., regions that are not electrically active). All of these elements, or a subset of these elements, may be displayed, so that a user may see a 3D heart model, an actual ECG waveform, and/or a virtual ECG waveform.

The correlation between the ECG waveform and its position on the heart may be calculated using the normalized heart vector and the direction of the lead vector $\vec{L}_0$, as described above. Thus, the electric potential $V_L$ in an arbitrary point on the patient's body, i.e., the value of the recorded lead signal, is given by formula (16). On the basis of this concept, one can obtain values $V_L$ for any other point, provided that the value of the vector $\vec{L}_0$ have the direction of the lead vector $\vec{L}$ that corresponds to the position of the point is known. The waveform is obtained using the equation (16) so that for values of the vector $\vec{L}_0$ that correspond to the angle coordinates of the point are used. In this example, the vector module of the hearth vector is set to the average value of the heart vector module for precordial leads $V_i$ to $V_6$. This means that waveform corresponds to virtual measurement points that would be positioned on a sphere having the same center as the heart model, with the radius corresponding to the average value of the radii of the precordial electrode measurement points (measured as an electrical distance, e.g., attenuation).

In any of the visual elements described herein, the user may magnify or "zoom" in or out of the image. For example, the user may zoom in on a region of the heart model, or a region of the ECG signal waveform. For example, the user may zoom out of an image of an actual or virtual waveform so that the time axis shows multiple PQRST waveform cycles; a single region in the time axis (e.g., corresponding to a single PQRST wave) may then be selected, zooming in on the image. When multiple waveforms are displayed, changing the scale of the time axis of one waveform may concurrently change the time axis on all of the waveforms displayed, or each waveform may have a different time axis scale. In some versions, the user may "scroll" through the time axis of one or more waveforms. The voltage axis of the ECG signal waveforms may similarly be controllable by the user and coordinated between the different waveform images.

The interactive display may be part of an ECG analyzer. For example, the ECG analyzer may include modules 3, 4, and 5 (in FIG. 1) as components of a single device. Thus, the ECG analyzer may receive ECG data, process the data, display the data, and respond to user commands. In some versions, the ECG analyzer includes a computer having components such as a monitor or other display device, and one or more command inputs (e.g., from a keyboard or mouse). In some versions, the ECG analyzer includes a computer running software supporting the described procedure of data processing and/or interactive visualization. Additional output devices (e.g., printers, electronic connections, digital storage media, etc.) may be used, for example, for reporting output or printing chosen screen shots obtained during the process of visualization.

An ECG analyzer may include a display (e.g., as part of a display module) or it may present data in a format that may be displayed by an additional device. In some versions, the ECG analyzer does not prepare the processed cardiac data for display, but provides the processed (e.g., normalized) data for storage, or for use by other devices or methods. For example, the ECG analyzer may process ECG data, normalize the ECG data, and present this ECG data to another device or tool. The normalized ECG data may be digital data, vectors, or waveforms, or as any other useful format.

Analysis Tools

The heart vector (including the normalized heart vector) may have a direction that is parallel to the direction of actual electric current across the heart. Thus, as current moves during cardiac electrical activity, the direction of the heart vector may reflect this movement. However, typical two-dimensional analysis of recorded ECG waveforms provides only a limited understanding of current flow across the heart. Thus, an analysis of the three-dimensional shape and motion of the heart vector may help interpret the electrical activity of the heart, and may provide new diagnostic tools and criterion. An Angle tool may be used to measure the angular difference in the heart vector over a selected time period.

Angle Tool (Heart Vector Spatial Angle Difference Tool)

The time varying heart vector reflects both the relative magnitude and the direction of the cardiac electrical activity of the heart. Thus, the direction of the heart vector changes over time, as may be seen from a heart vector hodograph, as previously described. An angle analysis tool, called an Angle tool (implemented in software in module 5), may be used to measure the difference in the angle between heart vectors in two or more time instants.

In general, the Angle tool compares the angle difference of two or more heart vectors. In one version, the user may interactively select two time points (e.g., from an ECG waveform) and the tool calculates the angular difference in the heart vector from those two time points. Interactive selection of the time points may be highly useful, because time points may be selected from displayed actual or virtual ECG waveforms. In some versions, automatic selection may be used (including waveform analysis to identify characteristic features). The tool may also analyze the heart vectors at the two specified times (or over the range of time). For example, the tool may calculate the variation in the angles of the heart vector over time, map the variation (e.g., differences) in the heart vector over this time. The tool may calculate any appropriate statistic, including but not limited to the rate of movement of the heart vector, the maximum and minimum differences in the heart vector, and the like. In some versions, the tool may display or otherwise provide statistical data. The tool may also display or provide graphical data. For example, the change in angle per unit time may be graphed and displayed, or the three-dimensional movement of the heart vector over the selected time range may be displayed, similar to the hodograph display previously described. As with all of the tools described here, data may be displayed, transmitted or stored.

In a Cartesian coordinate system, the angle between two heart vectors, A ($a_x$, $a_y$, $a_z$), and B ($b_x$, $b_y$, $b_z$), may be calculated from their orthogonal components ($a_x$, $a_y$, $a_z$ and $b_x$, $b_y$, $b_z$), from the following formula:

$$\cos(\alpha) = \frac{\vec{A}\cdot\vec{B}}{|\vec{A}|\cdot|\vec{B}|} = \frac{a_x b_x + a_y b_y + a_z b_z}{\sqrt{a_x^2 + a_y^2 + a_z^2}\sqrt{b_x^2 + b_y^2 + b_z^2}}$$

where α is the angle between the two heart vectors. The tool may determine the heart vectors A and B from specified time points (e.g., $t_0$ and $t_1$) using either a normalized or a non-normalized time dependent heart vector.

Analysis Tools for Identifying Cardiac Electrical Events

Presented herein are a series of approaches to precisely determine the time of cardiac electrical events and time intervals between such events.

Timing Cardiac Electrical Events Using the Heart Vector

As described herein, ECG data provides a time-dependent voltage that reflects electrical activity of the heart; multiple ECG leads sites provide different time-dependent voltage waveforms that reflect this overall electrical activity. From such data, a single time-dependent heart vector representing the heart's electrical activity can be calculated at any time point during the cardiac cycle. Any suitable method for determining the heart vector may be used. The heart vector and its hodograph may be presented to the viewer as 2D heart vector hodographs in orthogonal planes or as a 3D hodograph. The visualization module is suitable for this purpose.

The heart vector hodographs may be used to time cardiac electrical events by identifying the event on one or more heart vector hodographs, and correlating that event with events occurring at the same time point on one or more ECG leads (either ECG leads as actually recorded, or a virtual ECG lead). Alternatively, the cardiac electrical event can be identified on one or a plurality of ECG leads, and the temporally-correlated events identified on one or more heart vector hodographs.

Two or more display elements may be correlated so that when any time or spatial point is selected from one display, the selection (or change) is reflected in the other display or displays. Any time point may be selected. Such time points may indicate, for example, the following cardiac electrical events: $P_{on}$, $P_{end}$, $QRS_{on}$, $QRS_{peak}$, J point, $T_{on}$, $T_{peak}$, $T_{end}$, and the onset and end of the U wave ($U_{on}$ and $U_{end}$, respectively).

In some versions, the user may select a time value by interactively moving (or placing) a cursor on an ECG waveform. A specific cardiac cycle or cycles, or portions thereof, containing the electrical event of interest may be selected for detailed examination, for example by using marker lines to select all or part of a cardiac cycle of interest. Multiple cycles may be selected, and a composite 3D hodograph, or composite set of 2D hodographs, computed by any suitable method, e.g., averaging or subtracting. The composite hodographs may be used to identify cardiac electrical events in the same manner as set forth above.

The 3D heart vector hodograph may be rotated interactively, so that the screen displays the orientation where the desired cardiac electrical event is most effectively seen on the screen. This enables the viewer to identify more easily the cardiac electrical event of interest. For example, by rotating the 3D heart vector hodograph, the viewer could identify with precision the beginning of the T-wave heart vector loop. The viewer could then correlate the beginning of the T-wave heart vector loop with the corresponding time on an ECG, and thereby mark with precision the onset of the T-wave, $T_{on}$. Similarly, the viewer could use the 3D heart vector hodograph to identify and mark other cardiac electrical events, including but not limited to $QRS_{on}$, $QRS_{peak}$, the J point, $T_{peak}$ and $T_{end}$. The time interval between any two such events is calculated by simple subtraction.

Timing Cardiac Electrical Events Using the Angle Tool and Related Approaches

It is possible to measure the change in angular direction (angular change) in the heart vector over a selected time period. The Angle tool may be used for this purpose. Such measurement of angular change may be used to identify the time point in a particular section of the cardiac cycle where the heart vector changes direction more than a specified criterion. As one of many possible examples, the viewer could identify $T_{on}$ as follows: (1) define a time interval $\Delta t = t2-t1$ that begins late in the ST segment (ti) and ends in the upslope of the T-wave (t2); (2) determine angular change at a plurality of time points within Δt, for example using the Angle tool; (3) identify a time interval $t_\beta - t_\alpha$ within Δt wherein the angular change equals or exceeds a specified minimum, for example equal to or greater than about 5°, equal to or greater than about 10°, equal to or greater than about 20°, equal to or greater than about 30°, equal to or greater than about 45°, equal to or greater than about 60°, equal to or greater than about 90°, equal to or greater than about 120°, or more. $T_{on}$ is present within $t_\beta - t_\alpha$, and may be defined as any time point within that interval, if the specified minimum is equalled or exceeded. The optimal specified minimum for a particular cardiac event is determined empirically. Alternatively, the time of a cardiac event may be determined by finding $t_\omega - t_\delta$, defined as the time interval within Δt over which the heart vector exhibits a greater angular change than any other pair of time points within Δt.

Measurement of angular change in the heart vector, for example with the Angle tool, is particularly convenient to apply when Δt is a time range that includes the cardiac electrical event of interest, but is not so large as to include other cardiac electrical events associated with substantial angular changes in the heart vector. Continuing with the immediately preceding example, if Δt is selected to begin late in the ST segment and end in the upslope of the T-wave, it will include $T_{on}$. $T_{on}$ may be identified by determining the pair of time points $t_\beta - t_\alpha$ equalling or exceeding a specified minimum, or by identifying $t_\omega - t_\alpha$, or other suitable method. It is generally preferable to avoid choosing a substantially larger Δt, for example beginning before $QRS_{on}$ and ending after $T_{end}$, since Δt will then include several major changes in angular direction, thereby increasing analytical complexity and increasing the risk of ambiguity or error.

Since many important cardiac electrical events are associated with angular changes in heart vector direction, determination of such angular changes, for example using the Angle tool, is broadly useful in timing cardiac electrical events. For example, the Angle tool is highly effective in defining cardiac electrical events that are often difficult to identify visually or with other analytical tools.

Cardiac electrical events may also be identified by directional changes in functions derived from the heart vector function. One such approach is referred to herein as the Gamma tool. The angle γ is the angle between tangents of the trajectory of the heart vector $\vec{H}$ at two time points, that is where $\vec{H}=(X,Y,Z)=X\vec{i}+Y\vec{j}+Z\vec{k}$, and the first derivative of $\vec{H}$ is $$\vec{H}_t(t) = \frac{d\vec{H}(t)}{dt},$$

the angle γ is defined herein as:

$$\cos(\gamma) = \frac{\vec{H}_t(t1)\cdot\vec{H}_t(t2)}{\vec{H}_t(t1)\cdot\vec{H}_t(t2)} \quad (17)$$

where t1 and t2 are any two time points for which $\vec{H}_t(t)$ is available.

The angle may be used to identify the time point in a particular section of the cardiac cycle where the angle γ is greater than a specified criterion, for example equal to or greater than about 5°, or equal to or greater than about 10°, equal to or greater than about 20°, equal to or greater than about 30°, equal to or greater than about 45°, or more, as determined empirically. Alternatively, the time of a cardiac event may be determined by finding the time interval within Δt over which the angle γ exhibits a greater change than any other pair of time points within Δt. Thus, in a fashion similar to that described for the Angle tool, the Gamma tool may be used to determine the timing of a broad range of cardiac electrical events.

Another derived function from the heart vector function may also be used to time cardiac electrical events. This approach is referred to herein as the Kappa tool. The second derivative of the heart vector is $$\vec{H}_{tt}(t) = \frac{d^2\vec{H}(t)}{dt^2}$$

The value of Kappa, K (square of the curvature), at time point t can be calculated from the formula:

$$K(t) = \frac{(X_t^2 + Y_t^2 + Z_t^2)(X_{tt}^2 + Y_{tt}^2 + Z_{tt}^2) - (X_tX_{tt} + Y_tY_{tt} + Z_tZ_{tt})^2}{(X_t^2 + Y_t^2 + Z_t^2)^3} \quad (18)$$

The Kappa tool result, ΔK(t), is defined herein as the difference between the value of K(t) at two time points of interest, t1 and t2, in the cardiac cycle. The time points of interest may be, for example: t1, the approximate center of the downslope of the T-wave; and t2, a point apparently beyond $T_{end}$ but before the onset of the P wave, as identified visually. In this example, $T_{end}$ may be determined using the Kappa tool as a value of ΔK(t) equal to or greater than a specified minimum. Alternatively, the time of $T_{end}$ or other desired cardiac event may be determined by finding the time interval within Δt over which ΔK(t) exhibits a greater change than any other pair of time points within Δt. It is readily apparent that functions of the heart vector curvature similar to Kappa are also useful for identifying cardiac electrical events.

Timing Cardiac Electrical Events Using Virtual ECG Leads

For the purpose of timing cardiac electrical events, any recorded or standard ECG lead, or a plurality of such leads, are suitable. In addition, virtual ECG leads may be used, such as the heart vector magnitude or the normalized heart vector magnitude.

The heart vector magnitude VM=|$\vec{H}$|, may be calculated at any time point t in the cardiac cycle as:

$$VM=|\vec{H}(t)|=\sqrt{X(t)^2+Y(t)^2+Z(t)^2} \quad (19)$$

where X(t), Y(t), and Z(t) are the scalar values of the heart vector in the x, y, and z-axes, respectively, at time point t.

Figure 7:
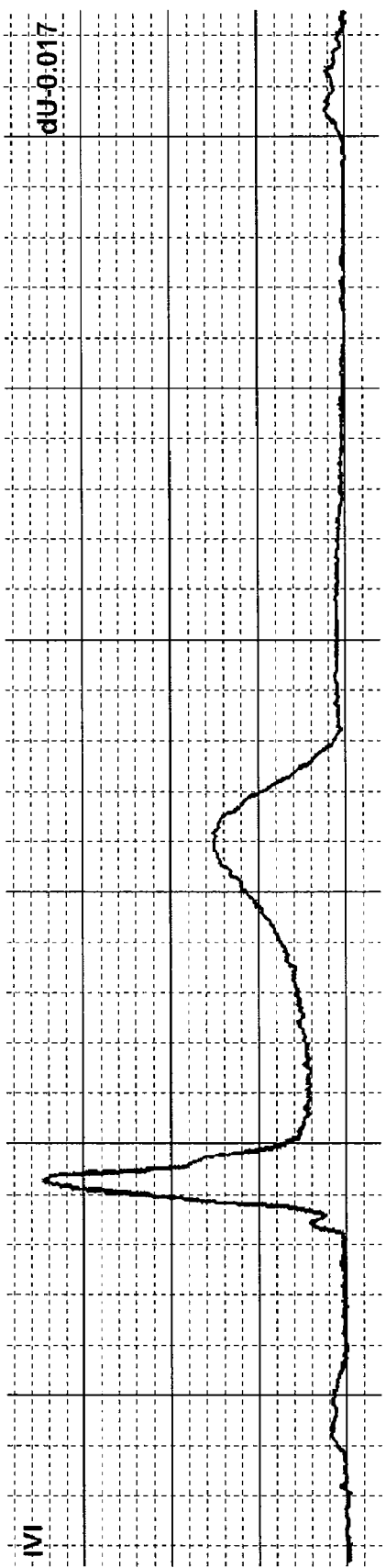
FIG. 7 shows an example of a vector magnitude tracing through approximately one cardiac cycle.
Figure 8:
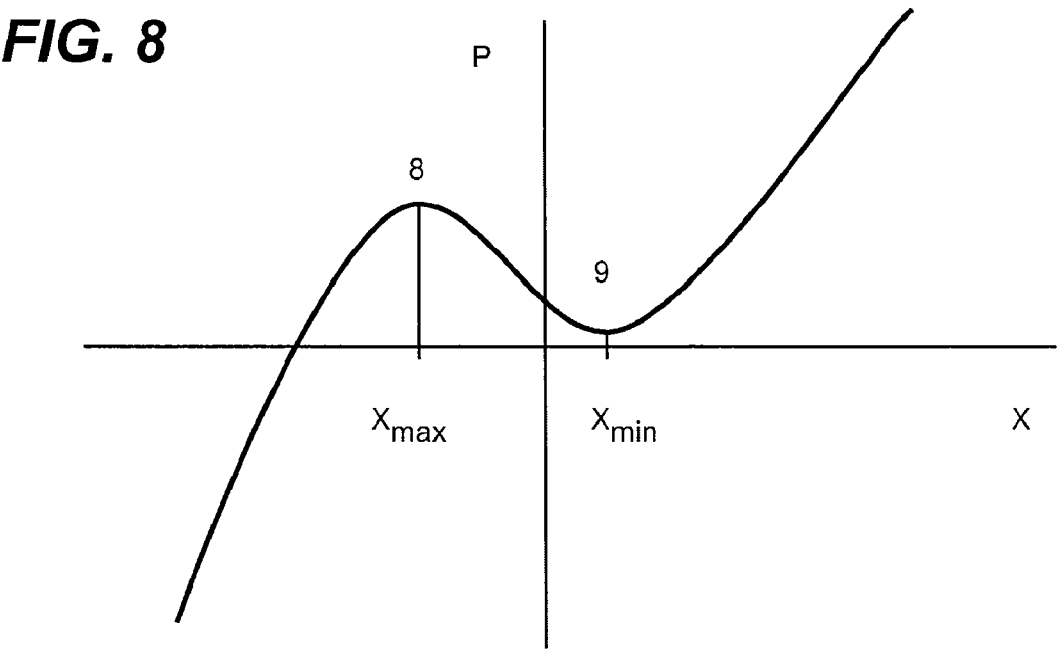
FIG. 8 shows an example graph of a $3^{rd}$ order polynomial function, with $X_{max}$ and $X_{min}$ indicated.
Figure 9:
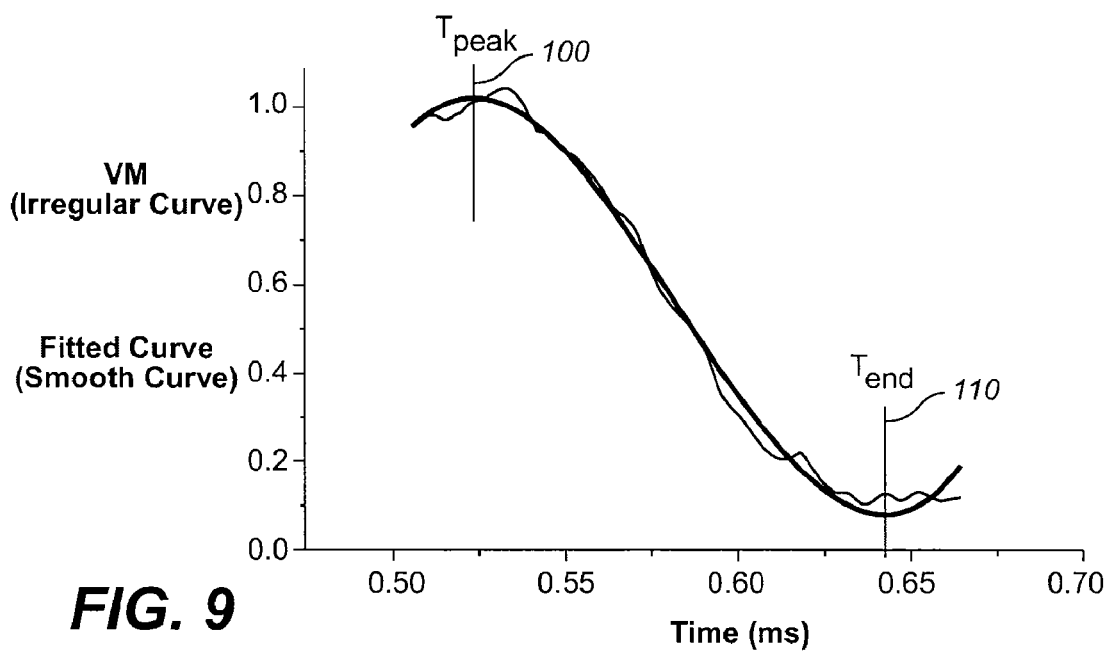
FIG. 9 shows an example of a vector magnitude tracing, with superimposed line indicating the results of curve fitting and identification of $T_{peak}$ and $T_{end}$ with a $3^{rd}$ order polynomial function.

FIG. 7 shows the value of VM over an entire cardiac cycle. VM may be viewed as a virtual ECG lead formed by contributions from all ECG leads used in calculating X(t), Y(t), and Z(t). Using virtual ECG leads such as VM to time cardiac events offers several key advantages over existing methods. The VM signal is larger than the signal in any recorded ECG lead, and has an overall improved signal to noise ratio. For example, the amplitude of the T wave can be very small, or negligible in some leads. If the T wave exists in any of the 12 leads, it will also exist in the VM signal. Moreover, unlike a recorded ECG lead, $T_{end}$ in VM cannot be artificially shortened by an orthogonal angle of the heart vector relative to the ECG lead late in the T-wave loop. As a consequence, the T wave duration in VM equals the T wave duration in the lead where this duration is the longest.

Other types of virtual ECG leads may be used to time cardiac electrical events. For example, one could use any virtual ECG lead described herein, such as normalized ST segment vector magnitude (NSTVM). One could also calculate a suitable virtual ECG lead by summing the voltages, or the absolute value of the voltages, from a plurality of ECG leads, for example, 2, 3, 4, 5, 6, 7, 8 or more ECG leads. Alternatively, a suitable virtual ECG lead could be calculated by multiplying two or more ECG leads by an arbitrary constant and calculating their sum, or the sum of absolute values. Another approach would be to determing the square root of the summation of squared recorded voltages from a plurality of ECG leads, e.g., $\sqrt{II^2+V_1^2+V_2^2...+V_6^2}$ for any two or more ECG leads, determined for at least that part of the cardiac cycle containing the events of interest, and preferably at least one cardiac cycle or more.

Another useful virtual lead finds its basis in the concept of the lead vector described by Burger et al, Brit. Heart J. 10:229, 1948. This virtual lead may be derived from the heart vector function by defining a unity vector as the components of the heart vector divided by Vector Magnitude, that is, at any time $t_0$, the components of the unity vector are $1_{0x}(t_0)=X(t_0)/VM(t_0)$, $1_{0y}(t_0)=Y(t_0)/VM(t_0)$, $1_{0z}(t_0)=Z(t_0)/VM(t_0)$ A virtual ECG lead, referred to herein as $V_{13}$, may be defined as the scalar product of the heart vector at that moment in time and the unity vector determined at the time of $QRS_{peaks}$, that is:

$$V_{13}(t)=l_{0x}(t_R)\cdot X(t)+l_{0y}(t_R)\cdot Y(t)+l_{0z}(t_R)\cdot Z(t) \quad (20)$$

where values for $l_{0x}(t_R), l_{0y}(t_R), l_{0z}(t_R)$ are all determined at the time of $QRS_{peak}$. V13 may be particularly useful for identifying cardiac electrical events associated with the QRS complex, for example $QRS_{on}$ and the J Point.

The $V_{13}$ virtual ECG lead may be derived as follows. Define tR as time when $QRS_{peak}$ is reached. At tR the components of the heart vector are: X(tR), Y(tR), Z(tR) and its magnitude is VM(tR). The direction of this heart vector is defined by unity vector: X0=X(tR)/VM(tR), Y0=Y(tR)/VM (tR) and Z0=Z(tR)/VM(tR). The $V_{13}$ virtual ECG lead is calculated at each point in time as the scalar product of the heart vector at that moment in time and the unity vector. This yields: $V_{13}(t)=X(t)*X0+Y(t)*Y0+Z(t)*Z0$.

The $V_{13}$ virtual lead may be used to define cardiac electrical events in the same manner as described herein for other virtual and recorded ECG leads. For example, a reference level for $V_{13}$ may be obtained using any of the methods described herein (particularly those described for defining a median isoelectric level) and the $V_{13}$ waveform fit to a third-order polynomial, using least squares or other suitable curve fitting method, in the time interval from $QRS_{peak}-2.5*DT$ to $QRS_{peak}-0.5*DT$ (where DT is determined using the V13 lead as the time from $QRS_{peak}$ to the next point on QRS which is less than or equal to half the voltage at $QRS_{peak}$).

Then, the minimum of the $3^{rd}$ order polynomial is found using a standard formula. Once the minimum is determined, the $QRS_{on}$ is found in the intersection between the polynomial and the reference level line to the left of this minimum, for example from the polynomial minimum leftward to $QRS_{peak}-4*DT$ Once the minimum for the $3^{rd}$ order polynomial is thus determined, one may then compare the $V_{13}$ function and the polynomial to the left of this minimum, for example from the polynomial minimum leftward to $QRS_{peak}-4*DT$. If the polynomial function crosses the reference level of $V_{13}$ in this interval, the user may choose to redefine $QRS_{on}$ as the time at which this intersection occurs, rather than the time at which the fitted polynomial function reaches a local minimum. In some instances, this adjustment may result in more accurate placement of QRSon.

From such examples, other suitable virtual ECG leads will be readily apparent to one of ordinary skill in the art. Such virtual ECG leads may offer some or all of the key advantages provided by VM, $V_{13}$ and others described herein in timing cardiac electrical events. This may result in more accurate and precise identification of cardiac electrical events than determinations from a standard ECG lead, or a plurality of such leads.

Timing of Cardiac Electrical Events Using Curve-Fitting Functions

Polynomial functions may be used to time key cardiac electrical events, such as $P_{on}$, $P_{end}$, $QRS_{on}$, J point, $T_{on}$, $T_{peak}$, and $T_{end}$. The methods will be illustrated below using a third order polynomial function, $P(t)=at^3+bt^2+ct+d$, but it will be readily recognized that higher order polynomial functions also may be used.

Polynomial interpolation may be used to determine values for the parameters (a, b, c, and d) that make the curve best fit a set of data points, using least squares or other suitable curve fitting method. For example, polynomial interpolation may be used to fit set of data points from any ECG lead. Alternatively, any virtual ECG lead such as VM may be used. The data points chosen for curve fitting can be, for example, points in or near the T-wave from any ECG lead, or from any virtual ECG lead.

For example, to determine the time of $T_{peak}$ and $T_{end}$ from VM, a section of VM is chosen visually or by computer analysis, the section extending from a time point after $T_{on}$ but at or before the apparent $T_{peak}$, to a time point at or after the apparent $T_{end}$. The section could be chosen to begin coincident with, or about 5 msec, or about 10 msec, or about 15 msec, or about 20 msec, or about 30 msec, or about 60 msec or more, before the apparent $T_{peak}$. The section could be chosen to end coincident with, or about 5 msec after, or about 10 msec after, or about 15 msec, or about 20 msec, or about 30 msec, or about 60 msec, more, after the apparent $T_{end}$. The section is then fitted to a third order polynomial using least squares or other suitable curve fitting method. $T_{peak}$ is then readily identified as the time point at which the third order polynomial function reaches a local maximum. Similarly, $T_{end}$ is the time point at which the third order polynomial function reaches a local minimum. In FIG. 3, such local maximum and minimum are identified as $X_{max}$ 80 and $X_{min}$ 90, respectively. In FIG. 4, $T_{peak}$ 100 and $T_{end}$ 110, as determined using the method described in this example, are indicated.

Other functions with one or more minima and one or more maxima are suitable for use in this method, and may be used to determine timing of cardiac electrical events, including, for example, $QRS_{on}$, the J point, $T_{on}$, $T_{peak}$, $T_{end}$, the beginning and end of U waves, and the beginning and end of the P wave. In addition to the third order polynomial, such functions include but are not limited to higher order polynomials, Legendre, Bessel, and Matheiu functions. (See Abramowitcz and Stegun, Handbook of Mathematical Functions, Dover Publications, New York, 1970.) Functions with one maximum or one minimum, such as a second-order polynomial, may also be used.

Defining a Median Isoelectric Level

When using vector based leads or a virtual lead such as Vector Magnitude (VM) or $V_{13}$ to evaluate cardiac electrical events, it is useful to define the magnitude of the heart vector with reference to an approximate isoelectric point or origin of the vector loop in three-dimensional space. Such a point is referred to herein as the reference point or alternatively, the reference level, which approximately corresponds to the voltage level of the isoelectric line (baseline) of ECG signals on a standard or virtual ECG lead.

When a time interval is displayed to an observer, the shape of VM, V13 or other virtual ECG lead may be affected by choice of the reference point. Since alterations in the shape of an ECG curve may in some instances affect timing of cardiac electrical events, it is useful to find a reasonably accurate and reproducible reference point. A reference point may be the common isoelectric baseline of 12 ECG leads. However, because of baseline wandering and electromechanical noise, determining a reference point in this manner can be difficult.

A reference point in 3D vector space that approximately corresponds to the isoelectric baseline level can be determined in the following manner. VM is used an example, but the approach is useful for any recorded or virtual ECG lead. VM is calculated at any time point t in the cardiac cycle with formula (19)

$$VM=|\vec{H}(t)|=\sqrt{X(t)^2+Y(t)+Z(t)^2}$$

where X(t), Y(t), and Z(t) (Frank leads) are the scalar values of the heart vector in the x, y, and z-axes, respectively, at time point t. These scalar values are defined as voltage differences:

$$X(t)=x(t)-x_0$$

$$Y(t)=y(t)-y_0$$

$$Z(t)=z(t)-z_0$$

where the point $x_0$, $y_0$, $z_0$, defines the reference point or approximate origin of the 3D vector loop, and corresponds approximately to the baseline of ECG signals.

Let the 3 vector ECG signals, x(t), y(t), z(t) be represented as a matrix V(i,j), index i representing the lead, and j representing the time instant (of n time instants). The overall range of the signals is divided in N segments in the following way:

Define maximal and minimal values of the signals in the whole matrix:

$V_{max} = max(V(i,j)) i=1,3; j=1,n$ $V_{min} = min(V(i,j)) i=1,3; j=1,n$

The $V_{min}$ to $V_{max}$ interval is divided in N segments (for example, N=10, or N=100, or N=1000, as desired) of approximately equal duration $dV=(V_{max}-V_{min})/N$ as:

1: $V_{min}$ to $V_{min}+dV$,

2: $V_{min}+dV$ to $V_{min}+2*dV, \ldots$ $\ldots$ and so on, to:

N: $V_{min}+(N-1)*dV$ to $V_{min}+N*dV$

For each of the 3 vector signals a distribution frequency function of signal points among these intervals is defined. For example, for the x vector signal, the number of signal points that fall within each interval is determined, that is, for the first interval, $V\min \leq V < V\min+dV$, the second interval $V\min+dV \leq V < V\min+2dV$, And so on to the last interval N.

Once the number of signal points that fall within each interval is determined, a distribution frequency function F ($x_n$) is determined, where F is the number of signal points of the matrix V(1,j) inside the interval $x_n$, and where x is the approximate mean value of the signal in a certain interval:

$x_n = V\min + i*dV - dV/2$

A reference level may be set to the approximate mean value of the signal corresponding to the maximum of the distribution frequency function F ($x_n$). Since F ($x_n$) is a discrete function whose precision may be limited by the number of discrete signal levels, one may use a continuous single peak function to approximate F ($x_n$). For example, F ($x_n$) may be fit to a Gaussian distribution $G=G0*\exp[-(x-x_0)^2/d]$, and the parameters G0, $x_0$ and d may be conveniently determined using least squares method. This approximation may be used to define the approximate maximum of the Gaussian distribution as a reference level for each signal V(1,j). A reference level determined with this procedure may be displayed to the observer as an approximately horizontal line, with the ECG or virtual ECG lead(s) being evaluated.

The above-described approaches for determining a reference level may be used on the whole available ECG signal including one or more heart beats, or may be used on a particular segment. For example, it may in some instances be advantageous to determine the reference level from a limited segment corresponding to the time interval from $T_{end}$ to $P_{on}$, or from $P_{end}$ to $QRS_{on}$. It may be used for determining reference levels for any recorded or virtual ECG lead, for example conventional 12 leads, vector-based leads, VM, $V_{13}$ and other virtual ECG leads.

Computer-Based Methods for Determination of QT Interval

Methods described herein may employ any of a variety of calculating platforms, such as a properly programmed personal computer, laptop, or handheld computer as module 5 of FIG. 1. For example, a desktop PC or laptop 5 with a Pentium III or equivalent processor 6, about 128 MB of RAM 10, a mouse or pointing device 9, and a monitor 7 would be suitable. Coding the software to be executed by the platform would be routine in light of this disclosure, using any convenient computer language. The software itself as stored on a computer readable storage medium such as memory 10 (in source code or compiled form) is also an article of manufacture, as well as being in its own right a computer enabled apparatus. Further, the present methods and system and apparatus may be embodied in the form of logic (hardware) in whole or in part rather than software or firmware. These methods are preferably carried out on a virtual ECG lead such as VM (whether normalized or not), $V_{13}$, or the like, but may also be applied to data from one or more ECG leads recorded from a subject.

Data recorded from the eight standard ECG leads can be described as a vector, $\vec{V}=(I, II, V_1, V_2, V_3, V_4, V_5, V_6)$. An approximate isoelectric level for each lead is determined by any suitable method. For example, the approximate isoelectric level may be determined using the methods described herein for determining a median isoelectric level, or by having an operator mark the approximate isoelectric level by visual estimation; or semiautomatically, by having an operator mark all or part of the T-P interval; or automatically calculating an average value; or by automatically locating a suitable segment of reasonably uniform voltage from the ECG data and calculating an average value for that segment.

The approximate isoelectric level for each lead is determined by any appropriate method and subtracted from the measured signals (e.g., $I'=I-I_0$, $II'=II'-II_0, \ldots V6'=V6-V6_0$) to yield $\vec{V'}=\vec{V}-\vec{V}_0$. The isoelectric-subtracted ECG data $\vec{V'}$ may be converted into a heart vector. Alternatively, the heart vector components (X, Y, Z) may be directly determined, for example by recording from the body surface with a Frank lead system. As an alternative, it is also possible to subtract the approximate isoelectric level from a virtual ECG lead such as VM.

In some embodiments, the operator may mark certain fiducial points on the ECG, such as the approximate peak of the QRS complex ($QRS_{peak}$), or the approximate $T_{peak}$, or both, on a monitor with a mouse- or keyboard-driven screen cursor. A computer-implemented algorithm may then calcualte $QRS_{peak}$ and $T_{end}$ by a suitable method by finding the local maximum of ECG data from the ECG lead, correcting any operator misplacement of $QRS_{peak}$ and $T_{peak}$ if necessary. In marking fiducial points, the operator marks the estimated point (e.g, $QRS_{peak}$, $T_{peak}$, or other desired point) anywhere within a time interval $\Delta t$ which contains the marked event. Usual values of $\Delta t$ may be about 2 msec, or about 5 msec, or about 10 msec, or about 20 msec, or about 50 msec, or about 100 msec, or more. In general, it is preferrable that the value of $\Delta t$ be set so as not to encompass a second maximum that exceeds the magnitude of desired event (for example, in determining $T_{peak}$, it is preferrable that $\Delta t$ is chosen so that it does not include $QRS_{peak}$).

Figure 10A:
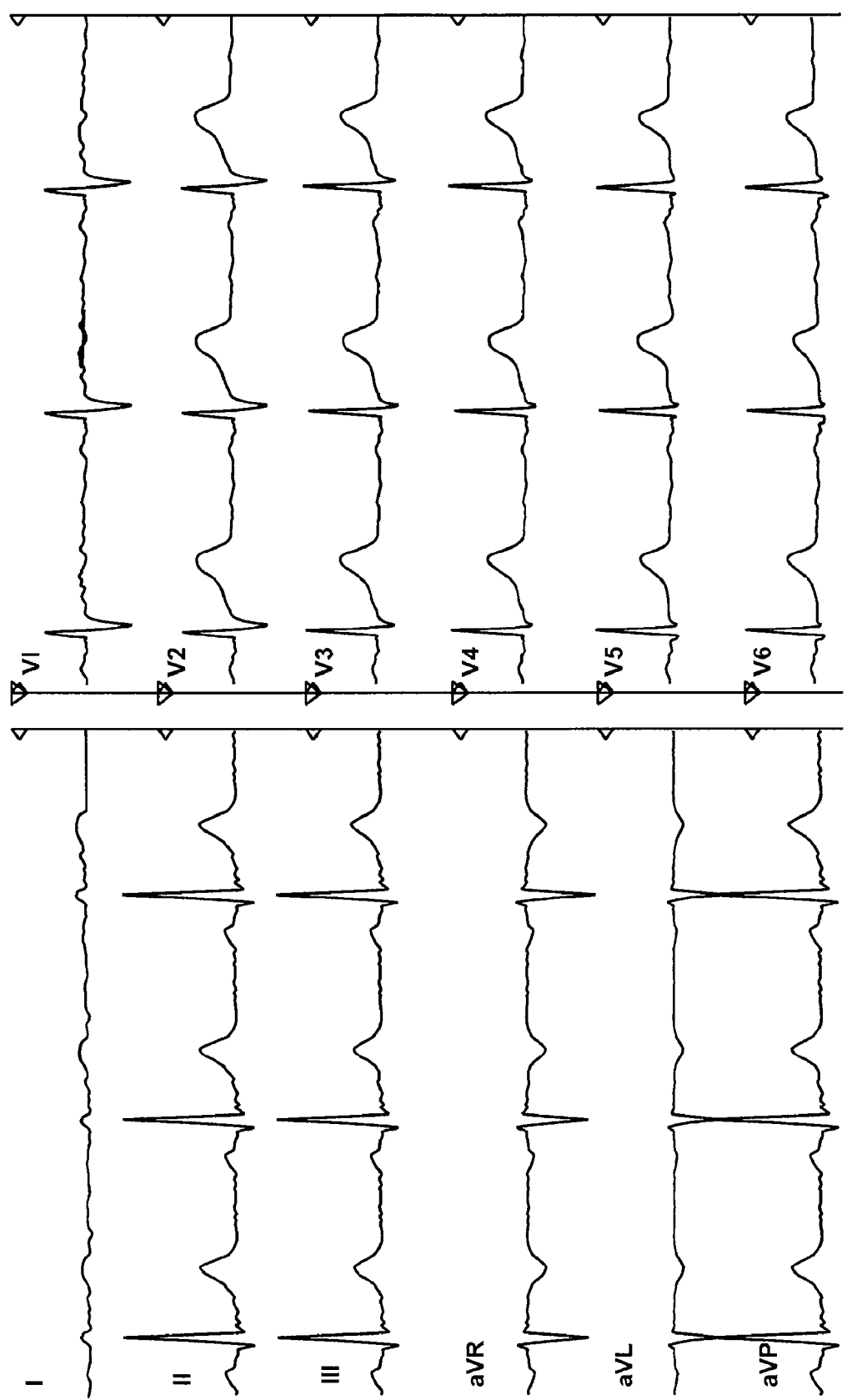
FIG. 10A shows an example of a 12-lead ECG, with FIG. 10B showing a vector magnitude tracing derived from the same input data as the 12-lead ECG of FIG. 10A.
Figure 10B:
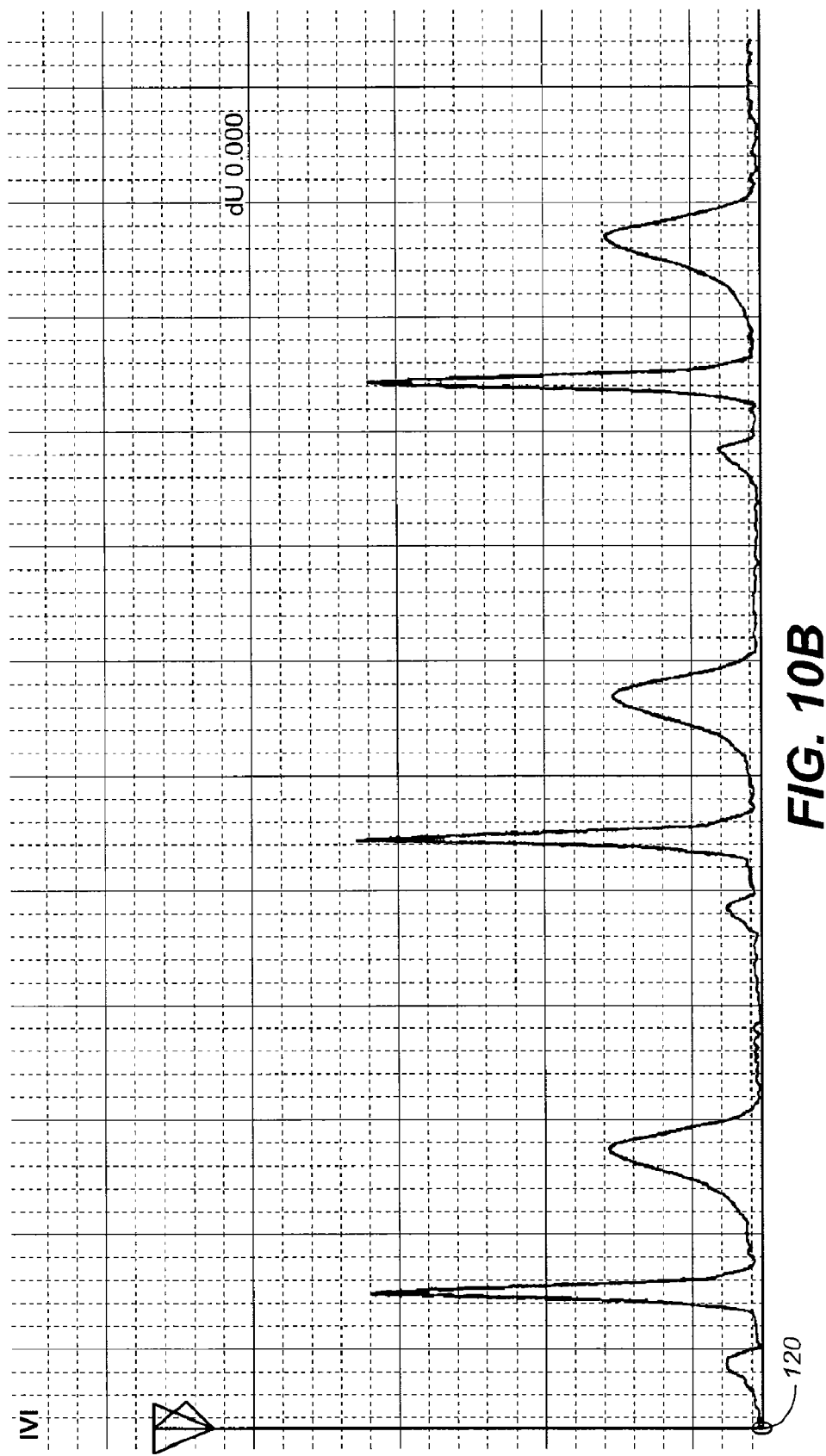

FIGS. 10A and 10B illustrate the operation of an embodiment for computer-based methods of QT determination. FIG. 10A illustrates a standard 12-lead ECG, obtained as a digital XML file from the Center for Drug Evaluation and Research, United States Food and Drug Administration, Rockville Md. FIG. 10B illustrates 3 beats of a virtual ECG lead, VM, calculated as described herein, using methods as disclosed herein. Reference level 120 is calculated automatically using the procedures described herein for determining a median isoelectric level.

Figure 11:
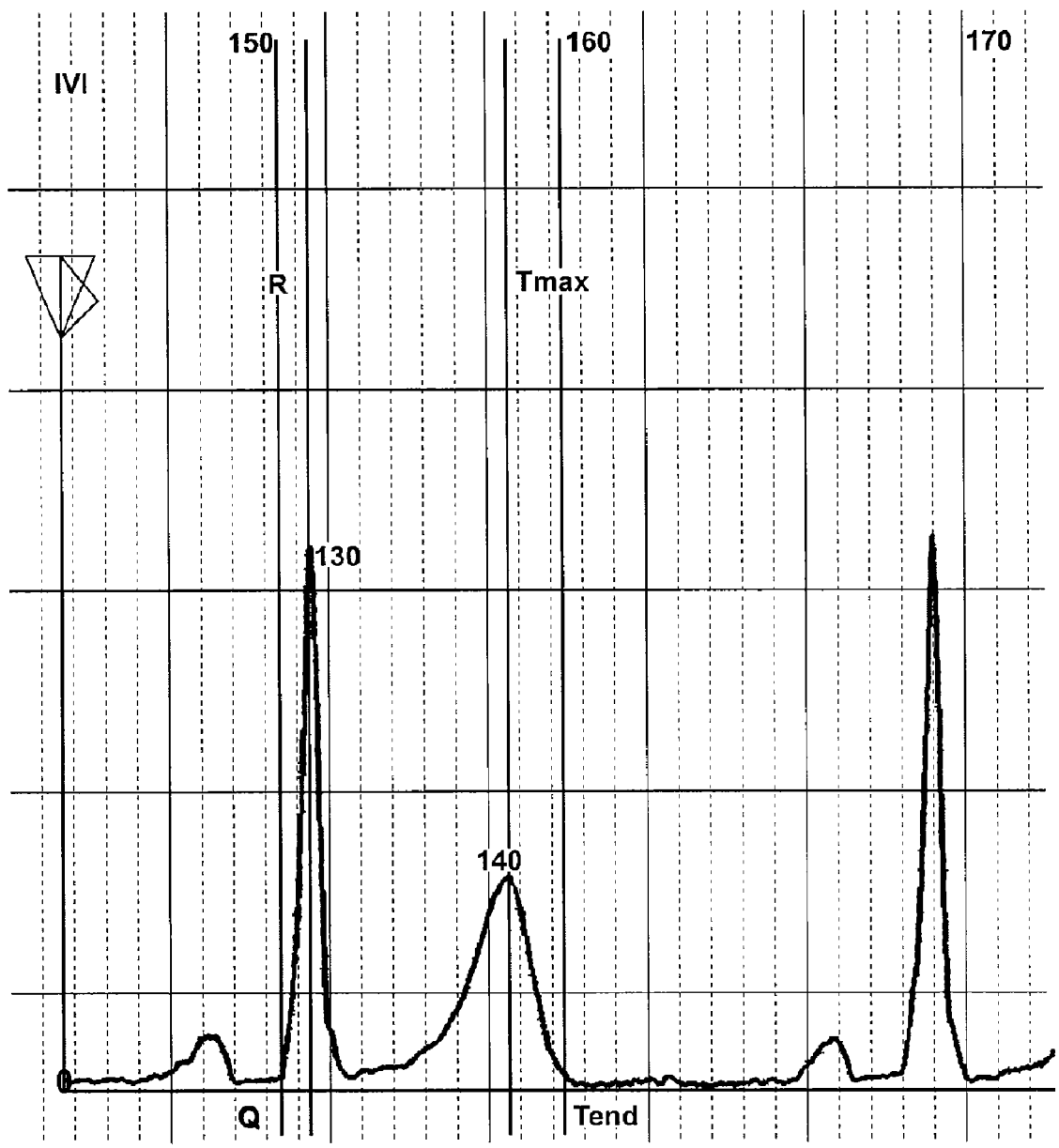
FIG. 11 shows the vector magnitude tracing, with the results of the calculated QT interval determination superimposed thereon.

In the example shown in FIG. 11, the user marks the approximate $QRS_{peak}$ 130 and $T_{peak}$ 140. The present method then employs the operator input to define the true $QRS_{peak}$ and $T_{peak}$, and proceeds to curve-fit using a third-order polynomial and least-squares curve fitting to define $QRS_{on}$ 150 and $T_{end}$ 160. The QT interval 170 is then calculated and displayed. The method may export the QT result and identifying information to another software program such as a conventional spreadsheet or database, and also may load the next ECG file, if a series of files needs to be read. Alternatively, the method as implemented in software may wait for further input, for example when an average QT for 2 or more beats is desired. Other calculations may also be performed, such as correction of the QT interval for heart rate, for example using Bazett's or Fridericia's formula, or other desired correction method.

Figure 12:
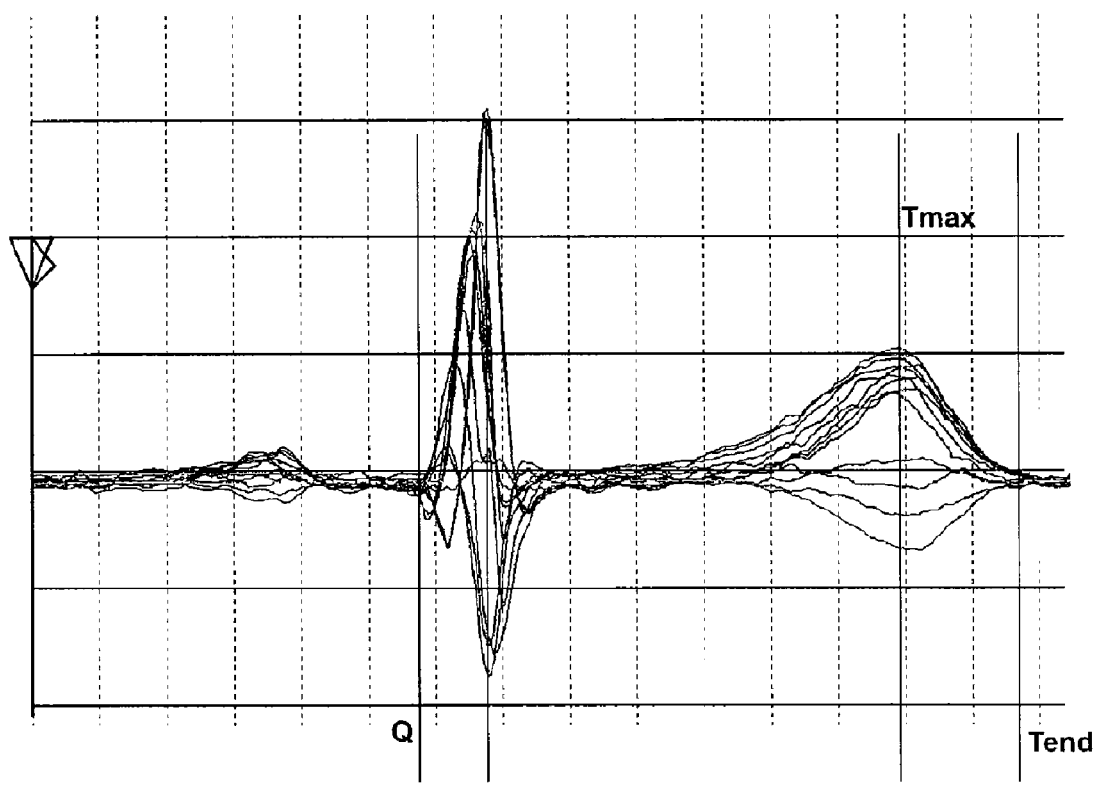
FIG. 12 shows an example of a global ECG lead, obtained from the same input data as the 12-lead ECG of FIG. 10A, with $QRS_{on}$, $T_{end}$, $QRS_{peak}$ and $T_{peak}$ superimposed thereon.

The accuracy of any calculated QT interval may be assessed by the operator in a variety of ways. For example, FIG. 12 shows a so-called "global" ECG lead, which is the superimposition of all 12 ECG leads on a single X-Y graph. The present method displays the location of the fiducial points, and the calculated $QRS_{on}$ and $T_{end}$, on the global lead. By assessing the location of $QRS_{on}$ and $T_{end}$ in relationship to the global lead, the operator can be assured that the caculated QT interval is reasonable and accurate.

Semi-Automated Identification of Cardiac Electrical Events

These procedures may be used with any ECG lead, particularly virtual ECG leads such as VM or $V_{13}$. Using a standard PC and monitor, handheld computer, or the like as explained above, an observer may display a suitable ECG waveform and mark a fidicuial point or points, for example the approximate $QRS_{peak}$, $T_{peak}$ or both. It is preferable to mark the point or points near the local maxima of the R and T waves. If there are multiple QRS peaks, it is generally preferable to mark the earliest peak (in a typical time-versus-voltage ECG display, the leftmost peak). Such multiple QRS peaks may be observed in conditions such as right bundle branch block, or if virtual leads such as vector magnitude are being used. If a T wave has multiple peaks, the observer may select the peak deemed most suitable, preferably following a predetermined and predictable set of rules to maximize reproducibility. Such a rule may be, for example, the leftmost $T_{peak}$ unless the rightmost $T_{peak}$ is more than half the amplitude of the leftmost peak.

Once the user has chosen an approximate fiducial point, the accuracy of placement of the fiducial point may be improved by the computer. For example, if the user has marked the approximate $QRS_{peak}$ or $T_{peak}$, a more accurate location of the $QRS_{peak}$ or $T_{peak}$ is defined as the local maximum in some time interval around the user-chosen point, for example the local maximum identified within 5 msec, or 10 msec, or 20 msec or more around the user-chosen point. The computed location of the fiducial point may be displayed to the user.

Once the desired fiducial points are established, they can be used to define subsequent points in the ECG that correspond to the fiducial points. For example, having established the location in time of the fiducial QRS peak R1, subsequent QRS peaks (R2, R3, etc) may be located by a variety of approaches. For example, determine the value $R_{0.5}=R/2$, or half amplitude of R1, and use $R_{0.5}$ to find the point $R_{0.5}*$ (point on the upslope of the next QRS complex) which is the first point to the right starting at $QRS_{peak}$+200 msec and having the amplitude greater or equal to $R_{0.5}$. The next $QRS_{peak}$, R2, is the local maximum in the interval $R_{0.5}*$, $R_{0.5}*$+100 msec. The RR interval is the time difference between R1 and R2 points. R3, R4, and subsequent QRS peaks may be found in a similar manner.

The fiducial points may also be used to refine reference levels. For example, the reference level may be redefined using the period of time between a $T_{peak}$ and the next $QRS_{peak}$, or in a similar time interval, for example $T_{peak}$+100 msec to $QRS_{peak}$−100 cosec. In such an approach, the distribution frequency function F ($x_n$) is limited only to those points falling within the selected time interval. Such a refinement may improve accuracy and reproducibility of certain cardiac electrical events, for example $T_{end}$, $U_{on}$, $U_{end}$, $P_{on}$ and $P_{end}$.

Fiducial points may be useful as landmarks to improve determination of cardiac electrical events. For example, $T_{peak}$ may be used to improve accuracy and precision in determining $T_{on}$, $T_{end}$, $U_{on}$, and $U_{end}$. One may define DT as the time interval between $T_{peak}$ and first subsequent point where the magnitude falls to less than half the magnitude at $T_{peak}$. Using DT, time interval boundaries for searching for $T_{end}$ with polynomial fitting may be defined as, for example, left boundary approximately $T_{peak}$−0.25*DT, right boundary approximately equal to $T_{peak}$+2.5*DT. It is readily apparent that a similar approach may be used to define time boundaries in which to search for other cardiac electrical events.

Once time boundaries are defined, curve fitting may be used to identify the desired event. For example, to find $T_{end}$, a third order polynomial may be fit to the ECG data within DT using a least squares method. In this method, $T_{end}$ would be identified as the local minimum of the third order polynomial Pt. By limiting the search to DT or other appropriate time interval, the chance for an erroneous determination is decreased.

The procedures described herein may also be fully automated in terms of no human operator being needed.

Evaluating Quality and Refining Estimates

When using the methods disclosed herein to determine the approximate time of a cardiac electrical event, the quality of a determination may be estimated. For example, when determining $T_{end}$ from the VM virtual lead, using a third-order polynomial curve-fitting, an estimate of quality may be obtained according to formula:

$$Tdiff[\%] = \frac{\sum_{i=2}^{N-1} |VM(t_i) - VMp(t_i)| + \frac{1}{2}[|VM(t_1) - VMp(t_1)| + |VM(t_N) - VMp(t_N)|]}{(N-1)|VM(t_1) - VM(t_N)|} 100$$

where VMp (ti) are the values of the third-order (Pt) polynomial, and the summation is done in the time interval between $T_{peak}$ and $T_{end}$. The quality estimate represents the weighted integral of the absolute difference between the polynomial and the original VM curve over the interval, and is approximately equal to the ratio of the surfaces of the difference Pt−VM(t) and the rectangle defined by $T_{peak}$ and $T_{end}$ points.

The observer may set boundaries of acceptability if desired. For example, the observer may establish as acceptable a value for Tdiff of 1%, 2%, 3%, 4%, 5%, 6%, 10%, 15%, or some other value. The determination is accepted if Tdiff is less than the boundary value, and rejected if greater than or equal to the boundary value. In instances where Tdiff exceeds the desired boundary value, the determination may be further refined by shifting the time of $T_{peak}$ rightward by a minimal amount, for example 1 msec or 2 msec, then repeating the $T_{end}$ calculation and redetermining Tdiff. If the boundary value is still exceeded, the time of $T_{peak}$ is again shifted rightward by a minimal amount and the calculations redone. This procedure continues until the boundary value is met, or some other cutoff is reached (for example, iterations to stop if the magnitude of $T_{peak}$ being used is less than 90%, or 80%, or 70%, or 60%, or 50%, or some other fraction of the original $T_{peak}$ value).

Determining the Onset and Termination of a QRS Complex

An accurate and reproducible determination of QRS onset ($QRS_{on}$) and its termination (J Point) is useful for determining cardiac time intervals such as PR interval, QRS duration, and QT interval. This example provides additional procedures for automated or semi-automated determination of $QRS_{on}$ and the J Point. They are particularly effective when used with virtual ECG leads such as VM, $V_{13}$ or the like.

Having determined $QRS_{peak}$, one can then determine the time between $QRS_{peak}$ and $QRS_{0.5}$, which is defined as first point prior to $QRS_{peak}$ where the magnitude of the VM curve falls to approximately less than 70% (or 60%, 50%, or some other desired value) of the magnitude at $QRS_{peak}$. This time interval is defined as DQ. If desired, an upper limit for DQ may be set, for example 50 msec, 60 msec, 70 msec, or some other value. If $QRS_{0.5}$ is not reached by the preset upper limit for DQ, then DQ is set at the said upper limit.

If desired one may define a new reference level using the time interval between $P_{end}$ end and $QRS_{on}$. This may be done, for example, by limiting the distribution frequency function F ($x_n$) to values in the interval from approximately [$QRS_{peak}$–4*DQ] to approximately $QRS_{0.5}$, or from approximately [$QRS_{peak}$–4*DQ] to any other desired point within the QRS complex. The values of VM or other ECG lead being used are adjusted according to the new reference level. This may adjust the reference point to the approximate level of the PQ segment (interval from $P_{end}$ to $QRS_{on}$), and may make it easier to accurately identify $QRS_{on}$. The location of $QRS_{on}$ may then be identified and marked by the user, or identified using a curve fitting technique such as fitting to a third-order polynomial or other suitable function.

Using Derivatives of the Heart Vector to Identify Cardiac Electrical Events

In physiologic terms, $QRS_{on}$ reflects the onset of ventricular depolarization, and the J Point reflects its end. These are a sudden and rapid events that are amenable to detection by examining changes in direction and speed of the heart vector. The same is true of several other cardiac electrical events, for example, $P_{on}$, $P_{end}$, $T_{on}$ and $T_{end}$.

Let X(t), Y(t), and Z(t) be components of a heart vector at time t:

$$\text{Heart Vector} = \vec{H} = (X, Y, Z) = X\vec{i} + Y\vec{j} + Z\vec{k}$$

Its magnitude at time t is $$VM = |\vec{H}(t)| = \sqrt{X(t)^2 + Y(t)^2 + Z(t)^2}$$

The heart vector velocity is the first derivative of the Heart Vector 43

$$\text{Heart Vector Velocity} = \overrightarrow{HVV} = dX/dt\ \vec{i} + dY/dt\ \vec{j} + dZ/dt\ \vec{k}$$

which approximately reflects the speed of movement of the point across the 3D loop in the 3D vector space. The magnitude of the heart vector velocity module is the square root of the sum of squares, that is, $$\text{HVV Magnitude} = HVVM = \sqrt{\left(\frac{dX}{dt}\right)^2 + \left(\frac{dY}{dt}\right)^2 + \left(\frac{dZ}{dt}\right)^2}.$$

Using HVVM within an appropriate time interval, for example beginning at $QRS_{peak}$ and proceeding leftward to $QRS_{peaK}$–4*DQ, $QRS_{on}$ may be identified as the first point with the value less than approximately 0.01 mV/sec, or less than approximately 0.02 mV/sec or similar desired threshold.

An empirically derived function, Velocity Attenuation, may be useful for determining $QRS_{on}$. Velocity Attenuation is defined as: VA=(1/HVVN$^2$)exp(–5·VM). Using VA, $QRS_{on}$ may be found as the first local maximum of the VA function greater than approximately 0.01 sec$^2$/mV$^2$, going from right to left in the approximate time interval $QRS_{peak}$ to $QRS_{peak}$–4*DQ (where DQ is determined as set forth above using $QRS_{0.5}$ of approximately 50%) or similar appropriate time interval. The J point may be found in similar fashion in the approximate time interval $QRS_{peak}$ to $QRS_{peak}$+4*DQ. It is readily apparent that functions similar to VA are also useful for identifying cardiac electrical events.

The second derivative of the heart vector, referred to herein as Heart Vector Acceleration (HVA), is also useful for identifying cardiac electrical events, particularly those in which acceleration is prominent, such as $QRS_{on}$ and J Point:

$$\text{Heart Vector Acceleration} = \overrightarrow{HVA} = \frac{d^2X}{dt^2}\vec{i} + \frac{d^2Y}{dt^2}\vec{j} + \frac{d^2Z}{dt^2}\vec{k}$$

The magnitude of HVA can be calculated as the square root of the sum of squares of its components in a manner similar to that used for VM and HVVM. The maximum magnitude of HVA in the approximate time interval $QRS_{peak}$ to $QRS_{peak}$–4*DQ may be used to identify $QRS_{on}$, or may be used to identify J point in the approximate time interval $QRS_{peak}$ to $QRS_{peak}$+4*DQ.

These methods are described primarily in terms of the QRS complex, but they are well suited to cardiac electrical events other than the QRS complex, for example $T_{on}$ and $T_{end}$.

Automated Selection of Optimal Complexes for Evaluation

In an ideal or nearly ideal ECG reading all complexes are very similar if not identical in their wave shape and complex duration (see FIG. 15). In the real life imperfections in ECGs are the rule rather than exception. Separation of the acceptable complexes from those that do not meet minimum quality standards is important for all applications involving automated ECG evaluation. Furthermore, even the methods that rely on creating a representative or median complex will benefit from selection of the optimal complexes that will be used for their creation.

The main criterion that will be used for multiple complex selection will be their similarity to each other. Noise and other distortion are typically either random phenomena (HF noise) or changes in baseline (LF noise). Both HF and LF noise and various one time random events typically will cause the wave shape of the affected complexes to change in a manner that is not repeatable and thus will cause these affected complexes to be different from one another. Another factor that contributes to dissimilarities is the duration of a complex as measured by the RR interval.

The basic complex selection method offered here relies on the fact that the repeatability of the complexes i.e. their similarity is the key for selecting a set of n best available complexes in an ECG having m total complexes. Both m and n are integers, and n may be any integer value between 1 and m. Typically n is equal to or greater than 2, but less than m. Preferably, n is 3, 4 or 5.

In order to select n complexes, one applies an autocorrelation function to all m complexes in the ECG being evaluated, as follows:

$$R_{ff}(\tau)=\bar{f}(-\tau)*f(\tau)=\int_{-\infty}^{\infty}f(t+\tau)\bar{f}(t)dt=\int_{-\infty}^{\infty}f(t)\bar{f}(t-\tau)dt$$

where $\bar{f}$ represents the complex conjugate and * represents convolution. For a real function, such as the ECG signal, $\bar{f}=f$.

The discrete autocorrelation R at lag j for a discrete signal $x_n$ is $$Rxx(j) = \sum_n x_n \bar{x}_n - j$$

The above definitions are suitable for signals such as the ECG signal that are square integrable, or square summable, that is, of finite energy.

If one desires, it is possible to evaluate the similarity of the complexes by a simplified approach. For example, one can look for a set of n complexes that has the minimum standard deviation between n complexes for some representative set of parameters, for example: peak voltage for T wave, peak voltage for QRS complex and the total area under the function formed by the ECG signal between two R points. The parameters chosen could be given equal weights or different weights. For example, the user may prefer to give the total area under the ECG curve more weight than other parameters chosen. For QT interval measurement applications, the user may desire to emphasize variability or standard deviation of QT values (or corrected QTc values) as an important parameter to select the most similar set of complexes for further analysis. For J-point selection, the user may prefer to emphasize variability or standard deviation of J point voltage values as an important parameter in selecting the most similar set of complexes.

The issue of which lead to use for applying the above described complex selection method is not a trivial one. One can apply the selection process to all 12 standard ECG leads, to the 8 measured leads, or any desired subset thereof The set of complexes that are the most similar can be then obtained by a selection function that would look for a logic AND function that is satisfied between the largest number of leads. It is also possible to make an appropriate selection by using a virtual ECG lead, such as VM or normalized VM. Such an approach has the advantage of containing information from all leads within a single virtual lead.

EXAMPLE

In this example, n is set to 3 and the above approach is applied to select the optimal 3 complexes to include. References to triplet in this example result from setting n equal to 3, but the term is intended to encompass all complexes chosen for inclusion in the analysis, e.g., if n had been set equal to 4, the term quadruplet would substitute for triplet.

DSFB is defined as the dissimilarity factor between complexes. It consists of 3 components:

a. SDTMAXT is the standard deviation for all maximum T wave voltages (Tmax) in a triplet. All possible triplets are ordered according to SDTMAXT. Each possible to triplet is assigned a rank according to SDTMAXT where the one with smallest SDTMAXT is ranked #1 (SDTMAXT rank=1) and so on.

b. SDRT is the standard deviation for all R voltages in a triplet

All possible triplets are ordered according to SDRT. Each possible to triplet is assigned a rank according to SDRT where the one with smallest SDRT is ranked #1 (SDRT_rank=1) and so on.

c. SDAAT is the standard deviation for all complex areas in a triplet. A complex area is defined as the total integral from peak R wave voltage to next peak R wave voltage. All possible triplets are ordered according to SDAAT. Each possible to triplet is assigned a rank according to SDAAT where the one with smallest SDAAT is ranked #1 (SDAAT_rank=1) and so on.

Once these components are determined, the complex dissimilarity factor DFSB can be calculated as:

DSFB=(SDTMAXT_rank+SDRT_rank+SDAAT_rank)/3

Although in the above description, each of the components is given equal weight, it is also possible to assign SDAAT 50% of the overall DSFB value, 30% to SDTMAXT, and 20% to SDRT, as determined empirically or as the user prefers.

DFSB is used together with the triplet SD QTc and other factors for triplet selection.

SDQTc_rank is assigned to every possible triplet in the ECG based on the triplet QTc SD. In general, the triplet with the smallest Triplet SDQTc will be ranked #1 etc.

SFT-Triplet selection function. Select triplet that has the smallest (but it must be >=1) value for SFT. Triplets with SFT=0 are eliminated. If no triplet has SFT>=1 set CIF=0 and output error message for the file "No acceptable triplet found"

SFT=CITBDMOVE_special*CITTDIFF*{QTC_weight*SDQTc_rank)+(DSFB weight*DSFB)}

Where:
QTC_weight=0.8 (default) and also in the CI tune params
DSFB_weight=0.2 (default) and also in the CI tune params
CITBDMOVE_special=0 if CITBDMOVE=0, and CITBDMOVE_special=1 in all other cases Confidence Index Any set of ECGs will have outliers that present difficult reading issues. An automated program for ECG assessment, for example cardiac interval determination, preferably should identify and "flag" such ECGs for manual overread. Described herein is a Confidence Index which represents a way of achieving this purpose. To simplify presentation of the analysis to the user, it is possible to report a Confidence Index score ranging from 0-99, or some similar range, where high scores indicate high confidence and low scores flag ECGs that should be manually overread. Those skilled in the art can readily see that a number of other reporting methods could be adapted as well.

Factors to include in a confidence index maybe empirically determined or chosen by the user. For example, possible factors that could be included to assess reliability of an automated read include: variability of the rhythm (for example, as measured by variability or standard deviation of RR intervals); variability of QT intervals or rate-corrected QT intervals; variability in voltages of cardiac events, such as peak R wave or T-wave voltages; low overall voltages, such as low T-wave voltage; unusual results for key cardiac intervals, such as unusually short or unusually long QT or rate-corrected QT intervals; QRS complexes exceeding a certain duration, for example exceeding 110 or 120 or 140 msec; J-point voltages or ST segment voltages that are unusually high or unusually low; substantial distortions or morphologic changes within the T-wave, such as, for example, biphasic shape or substantial distortions in the downslope of the T-wave.

Detection of Baseline Wander and Incorporation into the Confidence Index

Base line wander (BLW) is a phenomena that is most often associated with a high resistance path between an electrode and the skin. It results in a "carrier" signal upon which the useful ECG signal rides. Th frequency of the change of this carrier signal is low and typically ranges from 0.5 Hz to very low frequencies.

Baseline wander significantly reduces usefulness of the ECG signal and often causes diagnostic errors. For diagnostic biomarkers influenced by baseline level such as ST deviation, it can directly and significantly influence the result when standard ST deviation criteria are used. In other situations, such as QT interval measurements, it can influence in a significant and detrimental manner the results of a measurement, especially in the case of an automated method that uses the tangent or base line intersection methods for finding the end of a T-wave. Furthermore, it can significantly distort the median beat composition and thus be detrimental in the semi-automated methods for QT interval determination.

Thus, an effective automated program for ECG assessment should detect and account for BLW. The detection and the assessment of the magnitude of the BLW (that is, the amplitude of the low-frequency distortion/carrier signal) should be considered in the overall Confidence Index for a reading and specifically for the n beats that are being selected as the best in a given reading.

In order to detect BLW one can work in the 12 L classic ECG space or in the VM space. In either case for a given voltage reference point (baseline) one goes from beat to beat compares them in a similar manner to the beat selection for a set of n beats for QT measurement. In other words, the auto correlation function or one of its surrogates can be used to detect this phenomena. The absence of BLW is a necessary but not a sufficient condition for the beat similarity function to have a maximum. Accordingly, if the complexes selected in a reading exhibit high degree of similarity, BLW is absent or at least relatively limited. Other methods, relying a the concept of similar complexes can be applied. For example it is possible to compare the minimum voltage levels from all beats in a reading by measuring SD of their distribution. A high degree of variability minimum voltage levels for complexes chosen for the reading—measured, for example by the standard deviation of the minimum voltage levels—would lead to reduction in the overall CI and possible flagging of the ECG for manual overread.

EXAMPLE

As shown in FIG. 16, in this Example the CI begins with a weighted average of two classes of indicators: first, indicators that reflect the reliability of the triplet chosen for measurement (CI-Triplet, or CIT); second, indicators that reflect the quality and reliability of the ECG as a whole (CI-Entire Reading, or CIR). The relative weight given these two indicators is chosen empirically, and at present is 75% weight to CIT, 25% weight to CIR:

To obtain the final CI, the CIT-CIR weighted average is multiplied by a factor that is intended to reflect the overall functionality of the read. It is referred to as CIF (or CI-Functionality). At present, it is either 0 or 1. It is structured in this manner so that certain will automatically generate a flag suggesting a manual overread—hence their presence drives the CI to 0 regardless of any other features in the ECG.

In summary, then, the confidence index as contemplated in this Example is:

$$CI=CIF\times[0.75\times CIT+0.25\times CIR]$$

Another way to view the CI is beginning with CIF: that is, if CIF is 1, then CIT and CIR are determined, but if CIF is 0, the inquiry ends and the overall CI automatically assigned a value of 0, regardless of the value of CIT or CIR.

In this Example, CIF is conteplated as the indicator of basic functionality. It is determined from the triplet of complexes that QTinno selects for QT measurement. Its formula is: $CIF=(CIFB)_1*(CIFB)_2*(CIFB)_3*(CIFSDQTCT)$ The parameters that make up CIF include:

CIFSDQTCT. This is an indicator based on the standard deviation of QTc calculated from the triplet. If it exceeds the maximum range (set by the user), the value of this parameter becomes 0. The associated error message given to the user is "SD for the triplet is too high". The reasoning is that substantial variation in QTc between complexes in the triplet will flag the ECG for suggested manual overread.

CIFB. This is a multi-component parameter which is determined for each of the 3 beats in the triplet. It will be set to 0, and thereby cause overall CI to be 0, if any one of the complexes has defects that warrant manual overread of the entire ECG. It has the formula $$CIFB=(CIFTMB)*(CIFQTCVALB)*(CIFERRB)*(TDIFFB)$$

It is reduced to zero if any one of the following occurs:

(1) the T wave voltage in VM fails to exceed a minimum, adjustable by the user and currently set at 120 microV [CIFTMB] (error message "Low Tmax voltage");

(2) the QTc does not fall within an expected range, adjustable by the user and currently set at minimum 305 ms, maximum 490 ms [CIFQTCVALB=CIFQTCMINB*CIFQTCMAXB, where MINB is 0 if QTc is <305, and MAXB is 0 if QTc is >490] (error messages "QTc too short" or "QTc too long");

(3) the method returns an error message for processing the complex [CIFERRB; error message "Error in processing this beat"]; or (4) $T_{diff}$, a quantitative parameter that assesses the quality of QTinno curve fitting for Tend, exceeds a factor set by the user (currently 15%), indicating an imperfect fit [TDIFFB] (error message "Curve fitting for Tend not acceptable").

In this Example, CIT is intended to reflect factors affecting CI derived from the triplet (FIG. 16). It includes confidence factors derived from the selected triplet. Assuming CIF is given the value 1, CIT is presently assigned 75% weight in the overall CI.

There are two broad factors that affect CIT. The first is deformities in the latter part of the T-wave that exceed a a user-defined voltage threshold ("bumps"); the second relates to variability in QTc, RR interval, or Tend fit (as measured by variability in Tdiff). The formula is:

$$CIT=CITBDMOVE\times CITHFACTOR$$

CITBDMOVE. In general, the method defines $T_{end}$ by locating the maximum T-wave voltage $T_{max}$, then fitting the data from a user-defined time period after Tmax to a third order polynomial using using least-square fitting techniques. However, if in that time period QTinno program finds a "bump" on the downslope of the T wave, the maximum voltage of which exceeds a user-defined threshold (currently 20% of Tmax), QTinno then uses the "bump" as Tmax. If, within the triplet, no "bumps" are detected, or all 3 triplet complexes have "bumps", then CITBDMOVE is 1. However, if either 1 complex or 2 complexes have bumps, then CITBDMOVE is 0. The reasoning is that variations in T morphology leading to beat to beat uncertainty about the existence of "bumps" merits cardiologist overread in every instance. The associated error message is "Tmax moved to a different point."

CITHFACTOR. This factor reduces the overall CI if there is variability in QTc, RR interval, or Tend fit. Its formula is:

CITHFACTOR=100−CITSDQTC−CITSDRR−CITSDTDIFF

Where
CITSDQTC is a factor that increases as SD for QTc of the triplet increases, as follows:

| | |
|---|---|
| 0<Triplet SDQTc<=QTC_accept (msec) | CITSDQTC=0 |
| QTC_accept <Triplet SDQTc<= QTC_accept +1ms | CITSDQTC=1 |
| QTC_accept +1ms<Triplet SDQTc<= QTC_accept +2ms | CITSDQTC=2 |
| QTC_accept +2ms<Triplet SDQTc<= QTC_accept +3ms | CITSDQTC=4 |
| QTC_accept +3ms<Triplet SDQTc<= QTC_accept +4ms | CITSDQTC=8 |
| QTC_accept +4ms<Triplet SDQTc<= QTC_accept +5ms | CITSDQTC=16 |
| QTC_accept +5ms<Triplet SDQTc<= QTC_accept +6ms | CITSDQTC=32 |
| QTC_accept +6<Triplet SDQTc<= QTC_accept +QTC_range | CITSDQTC=64 |
| Triplet SDQTc> QTC_accept + QTC_range | CITSDQTC=100 and CIFSDQTC = 0. |
| Associated Error Message if CITSDQTC>0: "SD QTc higher than expected" | |

QTC_accept is user defined and currently set at 8 msec. Thus, an SD for the triplet of 8 ms or below will lead to no reduction in CITHFACTOR, and hence no reduction in CIT or overall CI. Above 8 ms, there is progressive reduction in these factors. Outside the QTC_range, however, the overall CI becomes 0 and manual overread is suggested.

| | |
|---|---|
| 0<SDRR<=SDRR_OK (SDRR_OK=3ms default) | CITSDRR=0 |
| SDRR_OK <SDRR<= SDRR_OK+1 | CITSDRR=2 |
| SDRR_OK+1<SDRR<= SDRR_OK+2 | CITSDRR=4 |
| SDRR_OK+2<SDRR<= SDRR_OK +3 | CITSDRR=8 |
| SDRR> SDRR_OK+3 | CITSDRR=16 |
| Associated Error Message if CITSDRR>0: "SD in the triplet is higher than expected" | |

As can be seen by comparing CITSDRR to CITSDQTC, in this Example the effect of variation in RR on CIT is not as marked as QTc variation, but has at least have some effect on CIT and the overall CI.

CITSDTDIFF is a factor that increases as SD for Tend fit quality factors (Tdiff) in the triplet increases, as follows:

| | |
|---|---|
| 0%<Triplet SDTdiff<=1% | CITSDTDIFF=0 |
| 1%<Triplet SDTdiff<=2% | CITSDTDIFF=2 |
| 2%<Triplet SDTdiff<=3% | CITSDTDIFF=6 |
| Triplet SDTdiff>3% | CITSDTDIFF=8 |
| Associated Error Message if CITSDTDIFF is >0: "Check Tend curve fitting" | |

In this Example, CIR reflects factors affecting overall CI equal to CIF×[0.75×CIT+0.25×CIR] derived from the ECG as a whole FIGS. 16A, 16B show determinatino of CIF and CIT. Assuming CIF is given the value 1 in this Example CIR is assigned 25% weight in the overall CI. Its components are: CIRBDMOVE is automatically assigned a value 0 if at least one, but not all, of the T waves have "bump" detected. It is similar to CITBDMOVE, except that it also includes complexes outside the selected triplet. A value of 0 would set the CIR component of CI to 0.

SD Components
a. SD RR—standard dev for all RR intervals in the reading
b. SD Tmax—standard dev for all Tmax voltages in the reading (before bump detector action)
c. SD R—standard dev for all R voltages in the reading
d. SD Tdiff—standard dev for all Tend fit quality factors
e. SD AA—standard dev for all beat areas (total integral from R to next R)
f. SD QTc—standard dev for all Corrected QT values in the reading
g. Number of Tmax points moved to a "bump"
h. Number of Tmax points not moved to a "bump"

The purpose of this factor is to reduce overall CI, and make flagging for manual overread more likely, as evidence accumulates that the ECG is less than optimally stable. This might result from arrhythmia, advanced cardiac disease, muscle artifact, poor electrode contact, baseline wander and the like. Any of these factors may suggest need for manual overread, even if the triplet itself receives a high CIT score.

EXAMPLE

This Example, shown in FIGS. 17A, 17B, 17C, illustrates an alternative approach to Confidence Index where CI=CIF×[0.70×CIT+0.30×CIR]. It differs from the previous Example in that different factors are brought to bear, and different weights are accorded to factors considered in the preceeding example.

CIF
Basic Functionality CI
=CIFB$_1$×CIFB$_2$×CIFB$_3$×CIFSDQTCT

Where CIFB$_n$ begins at 1 and is changed as follows with the following conditions:
Mult by 0.9 if voltage is 100-120 uV, 0.8 if 85-100 uV, 0.6 if 70-85 uV, and 0 if less than 70 uV,
Becomes 0 if QTc is <310 msec or >490 msec
Mult by 0.9 if QTc is 460-475 msec
Mult by 0.8 if QTc is 475-490 msec
Becomes 0 if there is an error message in processing the beat, or
Becomes 0 if Tdiff for a beat exceeds 15%

And CIFSDQTCT is
a value for SD of QTc for the selected triplet that exceeds a user defined threshold In this Example, overall CI is a function of CIF, CIT and CIR, as in the previous Example. Here, however, CIF may have a range of values between 0 and 1. One factor that may reduce CIF is low T-wave voltage as measured on the VM or normalized VM virtual ECG lead. CIF is reduced to 0.9, 0.8 and 0.6, progressively, as T wave voltage drops below 120 microV.

In this Example, CIT is influenced by CI–BLW, a parameter that reflects the presence and magnitude of baseline wander. Here, it is used as a multiplier in both CIT and CIR, though alternative approaches are available (for example, including it as a multiplier in CIF). In n this Example, no penalty (CI–BLW=1) is applied if BLW (measured here by SD of the minimum voltage levels) all is lower than a user chosen limit. The multiplier is progressively reduced, however, as the limit is exceeded. Very high variability in this or a similar parameter may lead to CI–BLW being reduced to as low as 0, thereby resulting in an overall CI of 0.

In this Example, CIT includes factors that reduce CIT if QRS duration or J point voltage exceeds a user-defined minimum.

CIT

Triplet Confidence Index

=CI–BLW×CITBDMOVE×CITHFACTOR

Where:

CI–BLW is 1 if SD of minimum voltage is in the triplet is less than a user-chosen limit; 0.9 in the limit is minimally exceeded; and progressively reduced to 0 in a user defined manner as the SD increases CITBDMOVE=0, if 1 or 2 bumps detected;

1 if 0 or 3 detected

CITHFACTOR=100–CITSDQTc–CITSDRR–CITSDTDIFF–QRS DURATION–J POINT VOLTAGE and components of CITHFACTOR are:

CITSDQTc increases if std dev for all QTc in triplet exceeds min value (8 msec); rises to 100 if QTc is >15 msec CITSDRR increases if std dev for RRs in triplet exceeds 3 msec, to a max value of 16

CITSDTDIFF increases if std dev for Tdiff exceeds a 1% threshold, up to a max of 18.

QRS Duration Score is 10 if mean QRS duration is 120 to 140 msec, 25 if 140-150 msec, 40 if 150-160, and 100 if >160.

J Point Voltage Score is 10 if J Point Voltage is 200-300 uV; 20 if 300-400; 40 if 400-500

Add points for high SD of QRS duration in triplet.

In this example, CIR has a factor that reduces overall score for evidence of baseline wander, and also includes factors that reduce overall score for high heart rate (for example, greater than 120/min or 140/min or 160/min, as chosen by the user), and for evidence of variability in QRS duration.

CIR

Whole ECG Confidence Index

=100–all SD components

SD components are:

SD RR for all RR intervals

SD Tmax for all Tmax voltages

SD R, std dev of all Rmax voltages

SD AA, std dev for all beat areas (RR integral)

SD QTc, std dev for all QTc in reading

SD QRS duration, std dev of all QRS durations in reading

SD–BLW is 0 if SD of minimum voltage for all complexes in the ECG is less than a user-chosen limit, and increases progressively in a user-defined manner as that limit is exceeded High Heart Rate, reduce CIR score by 20 if mean RR is less than 0.5 sec, by 40 if mean RR is less than 0.4 sec

EXAMPLE

Standard 12-lead ECGs (each approximately 10 seconds in length) were recorded in digital form from 26 healthy volunteers at 4 different times: at baseline, and at 1, 2 and 3 hrs after ingesting a drug known to affect cardiac electrical events. These 104 "study" ECGs were read manually by two trained and experienced readers, and in parallel by devices and computer software incorporating methods disclosed herein, and the results were compared.

For manual reading, the Study ECGs were displayed in random order on a high-resolution computer monitor to two cardiologists, working independently and unaware of the other's results. Readers marked $QRS_{on}$, $QRS_{peak}$, $T_{peak}$, and $T_{end}$ on 5 successive QRS complexes that they judged to be the most suitable for analysis. One of the observers repeated the analysis approximately 10 days later, with Study ECGs reordered and without knowledge of prior results.

Semi-automated reading was performed using software, as disclosed herein. A VM virtual lead was derived for each of the Study ECGs, and displayed in random order on a high-resolution computer monitor to two readers working independently and unaware of the other's results. For each VM trace, the readers marked the approximate peak of a QRS complex and the approximate peak of the T wave following the selected QRS complex. The $QRS_{peak}$ and $T_{peak}$ closest to the user marks were then determined in automated fashion, as were the next 4 successive $QRS_{peak}$ and $T_{peak}$. For each QRS complex, $QRS_{on}$ was identified using methods described for semi-automated determination of cardiac electrical events and for determining the onset and termination of a QRS complex. Results were displayed in graphic fashion to the user, and numerical results exported to a spreadsheet. Intervals were then calculated, including RR and QT intervals, $Q_{on}$ to $T_{peak}$, $T_{peak}$ to $T_{end}$. QT intervals were corrected for heart rate using Fridirecia correction. Upon user approval, the next ECG was automatically loaded and presented to the reader, and the process repeated. One of the observers repeated the analysis approximately 10 days later, with Study ECGs reordered and without knowledge of prior results.

Results obtained with manual and semi-automated readings were compared. The present method was considerably faster in performing the task than manual readers. The total time to read one set of Study ECGs was approximately 2.5-3 hrs for manual reading, and 15-20 min using the present semi-automated method. On average, this was over 90 sec per ECG during manual read, and less than 10 sec for semi-automated read.

TABLE 3

Cardiac intervals determined with manual and semi-automated measurements

|  | Manual (msec ± SD) | QTinno (msec ± SD) |
|---|---|---|
| Mean RR Interval | | |
| Baseline | 952 ± 145 | 946 ± 143 |
| 1 hr after drug ingestion | 1045 ± 126 | 1045 ± 129 |

TABLE 3-continued

Cardiac intervals determined with manual and semi-automated measurements

|  | Manual (msec ± SD) | QTinno (msec ± SD) |
|---|---|---|
| 2 hrs after drug ingestion | 1086 ± 143 | 1093 ± 140 |
| 3 hrs after drug ingestion | 1104 ± 138 | 1097 ± 143 |
| Mean QT Interval | | |
| Baseline | 379 ± 20 | 377 ± 22 |
| 1 hr after drug ingestion | 405 ± 22 | 404 ± 24 |
| 2 hrs after drug ingestion | 432 ± 23 | 432 ± 22 |
| 3 hrs after drug ingestion | 436 ± 27 | 439 ± 24 |
| Mean QTc (Fridericia) | | |
| Baseline | 390 ± 16 | 385 ± 19 |
| 1 hr after drug ingestion | 405 ± 21 | 400 ± 25 |
| 2 hrs after drug ingestion | 423 ± 22 | 421 ± 24 |
| 3 hrs after drug ingestion | 426 ± 26 | 424 ± 25 |

The data in Table 3 show the mean cardiac intervals obtained. In each instance, the figure is the mean±standard deviation of 104 determinations (26 determinations made a total of 4 times, 2 times each by 2 observers). Shown are results for RR intervals, QT intervals, and Fridericia-corrected QT intervals (QTc) obtained with manual and semi automated readings.

As may be seen from data in Table 3, the two approaches also returned very similar values for the mean prolongation of QTc produced by the drug. Relative to baseline, mean increase in QTc was estimated at 15 msec at 1 hr by both Manual and QTinno; at 2 hrs, 33 msec for Manual and 36 msec for QTinno; and at 3 hrs, 36 msec for Manual and 38 msec for QTinno.

Figure 13:
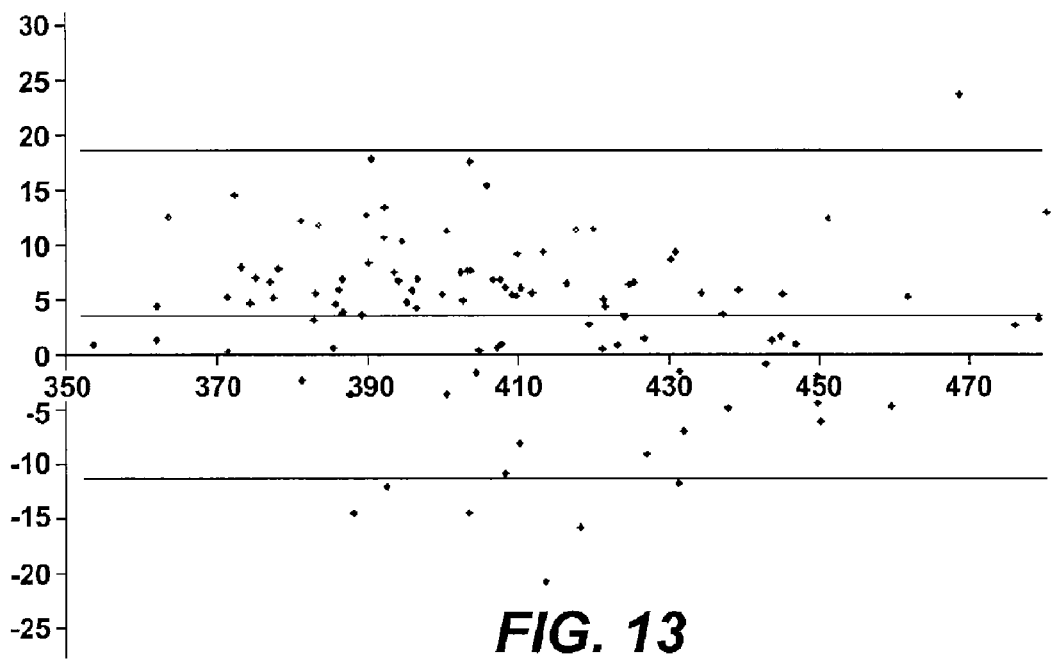
FIG. 13 shows a Bland-Altman plot of corrected QT intervals obtained using manual and semi-automated measurements.

FIG. 13 shows a Bland-Altman analysis of QTc determined by manual and semi-automated methods. Each point on the plot represents an individual determination. The x-axis is the average QTc value of manual and semi-automated determination, in msec. On the y-axis, points on which manual and semi-automate methods returned the same value lie at 0, points where manual returned a higher value are positive, and points where manual returned a lower value are negative. On average, manual determinations were 3.7 msec higher than semi-automated, with a SD for differences of 7.4 msec.

These data show that the semi-automated approach returned results that were closely matched to the "gold standard" of careful manual reading by trained cardiologists, but did so much faster and in a much less labor-intensive manner.

When individual determinations were examined, it was apparent that the precision of semi-automated measurement was substantially higher than for manual measurement. In determining intervals, whether by semi-automated or manual methods, each subject had a total of 15 determinations made. For each interval, a mean and standard deviation was calculated for the 15 determinations. This yielded a total of 104 standard deviations, for which a mean was determined.

TABLE 4

Mean SDs of cardiac interval measurement

|  | QT | RR | QTc |
|---|---|---|---|
| Manual | 7.2 msec | 52.4 msec | 8.7 msec |
| Semi-automated | 3.4 msec | 51.6 msec | 5.5 msec |

Figure 14A:
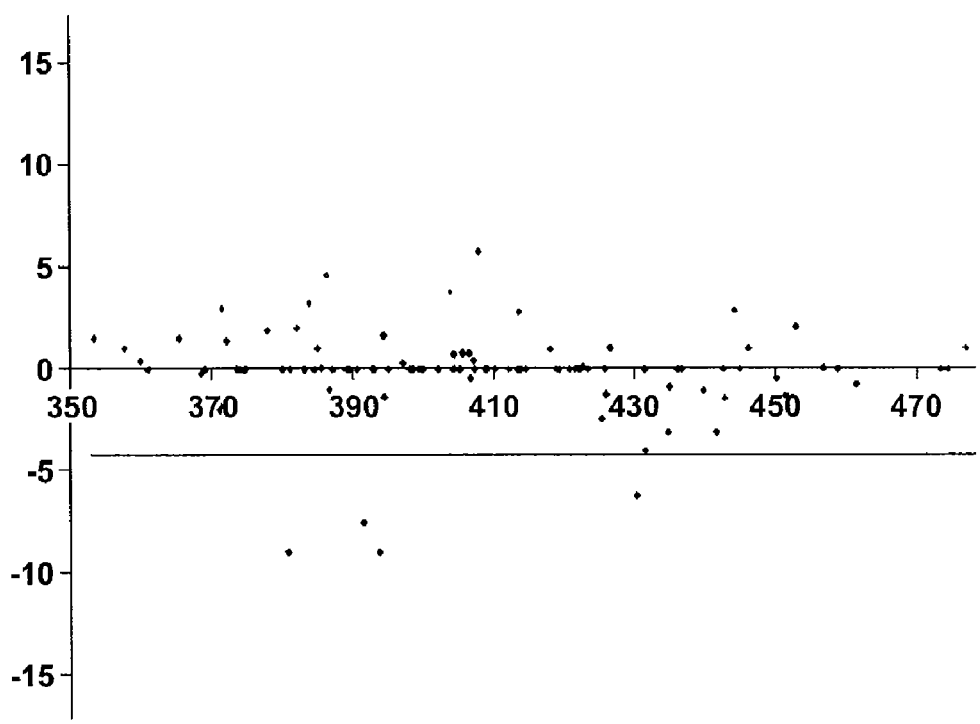
FIG. 14A shows a Bland-Altman plot of interobserver variability of corrected QT intervals obtained using semi-automated measurements.
Figure 14B:
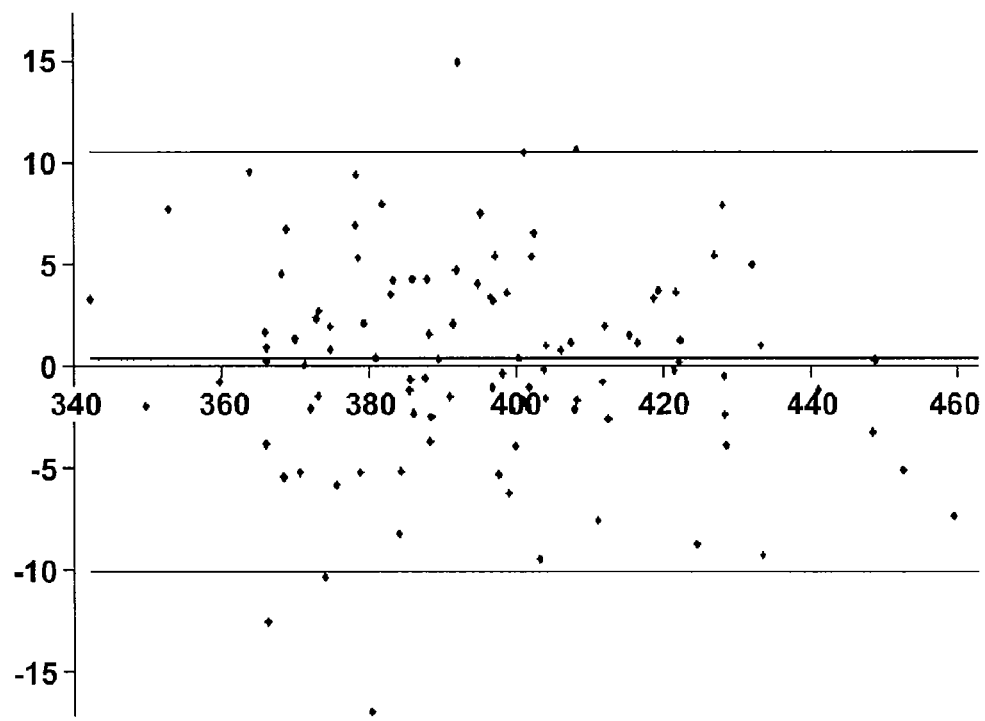
FIG. 14B shows a Bland-Altman plot of interobserver variability of corrected QT intervals obtained using manual measurements

Table 4 shows that the mean SDs for QT and QTc were far lower using semi-automated measurements than using a manual approach. Thus, not only was the semi-automated approach faster and easier, it was also more precise and reproducible. This conclusion is reinforced by the data in FIGS. 14A and 14B, which compares Bland-Altman plots for QTc determined by different observers. For semi-automated measurement in FIG. 14A, the mean interobserver difference in QTc was 0.1 msec with a SD of 2.1 msec. Of 104 determinations, 56 were identical and 98 were within 4 msec of each other. For manual reading in FIG. 14B, the mean interobserver difference was 0.3 msec with a SD of 5.0 msec—over two-fold higher than that obtained with semi-automated measurement. Only 1 of 104 determinations was identical, and 36 were different by more than 4 msec.

The greater precision obtained using semi-automated measurement is highly important for clinical diagnosis and for drug safety analysis. For example, the number of subjects needed in a clinical study of drug effects may be calculated according to equation (18):

$$n = 2(Z_\alpha + Z_\beta)^2 \times \frac{S^2}{(\mu_1 - \mu_2)^2} \quad (18)$$

where n is the number of subjects needed, $Z_\alpha$ is the desired significance level, $Z_\beta$ is likelihood of beta error, $\mu_1 - \mu_2$ is the expected drug effect on the parameter being studied, and S is the standard deviation for the parameter being measured. Thus, a 2-fold improvement in measurement precision, as measured by S, will result in a 4-fold reduction in n. In a study of drug effects on QTc, the lower SD obtained by semi-automated measurement, shown in Table 4, would reduce the number of subjects needed by 2.5-fold.

Although the methods, articles of manufacture, systems, and devices described herein are directed to devices and methods for timing cardiac electrical events, the invention should not be limited to timing cardiac electrical events, and should apply to the analysis, diagnosis or treatment of any cardiac electrical phenomena (for example, abnormalities in cardiac electrical conduction processes, disturbances of heart rhythm or dysrhythmias, location of accessory pathways and reentrant circuits, infarction, cardiomyopathy, cardiac hypertrophy, etc.).

Further, although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Furthermore all references cited herein are intended to be fully incorporated herein in their entirety.

The invention claimed is:

1. A computer-assisted method for selecting ECG complexes for further evaluation, the method comprising:
   receiving a recorded patient ECG signal comprising a plurality of m ECG complexes; and
   using a processor to evaluate ECG complexes of the plurality of m ECG complexes, and to identify a subset of n ECG complexes of the plurality for further evaluation, where n is greater than two and less than m, and wherein the n ECG complexes of the identified subset have a highest degree of similarity to one another relative to any other possible subset of n ECG complexes of the plurality of m ECG complexes.

2. The method of claim 1, wherein the identified subset of n ECG complexes is identified by applying an autocorrelation function to the m ECG complexes of the plurality of ECG complexes.

3. The method of 2, wherein the autocorrelation function is $$\int_{-\infty}^{\infty} f(t+\tau)\overline{f}(t)dt \text{ or } \int_{-\infty}^{\infty} f(t)\overline{f}(t-\tau)dt$$

where τ is an increment of time t, f is a function and $\overline{f}$ is the complex conjugate of function f.

4. The method of claim 1, wherein the identified subset of ECG complexes is identified from virtual ECG data derived from the recorded ECG signal.

5. The method of claim 4, wherein the virtual ECG data is vector magnitude data or normalized vector magnitude data.

6. The method of claim 1, wherein the identified subset of n ECG complexes is a first identified subset of n ECG complexes, the method further comprising:
   determining a first value of a complex dissimilarity factor for the first identified subset of n ECG complexes;
   identifying from the plurality of m ECG complexes a second subset of n ECG complexes, wherein the second identified subset has at least one ECG complex that than is not part of the first identified subset;
   determining a second value of a complex dissimilarity factor for the second identified subset; and
   if the second value is less than the first value, selecting the second identified subset for further evaluation instead of the first identified subset.

7. A computer-assisted method for selecting ECG complexes for further evaluation, the method comprising:
   receiving a recorded patient ECG signal comprising a plurality of m ECG complexes, each ECG complex of the plurality having a duration; and
   using a processor to evaluate ECG complexes of the plurality of m ECG complexes, and to identify a subset of n ECG complexes for further evaluation, where n is greater than two and less than m, and wherein the n ECG complexes of the identified subset have a lowest standard deviation in duration out of all possible subsets of n ECG complexes of the plurality of m ECG complexes.

8. A computer-assisted method for selecting ECG complexes upon which to evaluate cardiac events, the method comprising:
   receiving a recorded patient ECG signal comprising a plurality of m ECG complexes;
   using a processor to evaluate a respective same electrical event in each ECG complex of the plurality of m ECG complexes; and
   using a processor to identify a subset of n ECG complexes of the plurality of m ECG complexes, where n is greater than two and less than m, wherein the ECG complexes of the identified subset have a lowest standard deviation in the evaluated electrical event out of all possible subsets of n ECG complexes of the plurality of m ECG complexes.

9. The method of claim 8, wherein the electrical event is a time interval selected from the group consisting of:
   duration of the ECG complex,
   PR interval,
   RR interval,
   QT interval,
   rate-corrected QT interval,
   time interval between Tpeak and Tend,
   time interval between QRSonset and J point,
   time interval between Ponset and Pend, and
   time interval between peak voltage for R wave and peak voltage for T wave.

10. The method of claim 8, wherein the electrical event is a voltage selected from the group consisting of:
   peak voltage for T wave,
   peak voltage for R wave,
   peak voltage for P wave.

11. The method of claim 8, wherein the identified subset of n ECG complexes is a first identified subset of n ECG complexes, the method further comprising:
   determining a first value of a complex dissimilarity factor for the first identified subset of n ECG complexes;
   identifying from the plurality of m ECG complexes a second subset of n ECG complexes, wherein the second identified subset has at least one ECG complex that is not part of the first identified subset;
   determining a second value of a complex dissimilarity factor for the second identified subset; and
   if the second value is less than the first value, selecting the second identified subset for further evaluation.

* * * * *